(12) United States Patent
Smikodub

(10) Patent No.: US 6,184,033 B1
(45) Date of Patent: Feb. 6, 2001

(54) MEDICINAL PREPARATION BASED ON FETAL CELL SUSPENSION HAVING IMMUNE SUBSTITUTING EFFECT FOR PATIENTS WITH ACQUIRED IMMUNE DEFICIENCY SYNDROME (HIV INFECTION)

(75) Inventor: Alexandr Ivanovich Smikodub, Kiev (UA)

(73) Assignee: Centr Embrionalnikh Tkaney "Emcell", Kiev (UA)

( * ) Notice: Under 35 U.S.C. 154(b), the term of this patent shall be extended for 0 days.

(21) Appl. No.: 09/156,258

(22) Filed: Sep. 18, 1998

Related U.S. Application Data

(63) Continuation-in-part of application No. 08/505,236, filed on Aug. 9, 1995, now Pat. No. 5,811,089.

(30) Foreign Application Priority Data

Dec. 14, 1993 (UA) .................................................. 94061620

(51) Int. Cl.⁷ ...................................................... C12N 5/00
(52) U.S. Cl. .......................... 435/366; 435/372; 435/375; 424/93.1
(58) Field of Search .................................... 435/366, 372, 435/375; 424/93.1

(56) References Cited

PUBLICATIONS

Petrasincu et al. "Methodological Model of Handling a Newly Isolated Human Diplaoid Cell Strain and Its Surveillance," Archives Roumaines de Pathologie Experimentale et de Microbiologie, vol. 36, No. 1, pp. 49–54, 1977.*

Kitazawa et al. Granulocyte–Macrophage Progenitor Cells in the Liver of Human Embryo and Fetus. Acta Haemotol Japan, vol. 48, No. 6, pp. 1341–1349, 1985.*

Petrov et al. "Colony–forming Capacity of Precursor Cells of Granulomonopoiesis in the Liver and Spleen at Different Stage of Human Embryo and Fetogenesis," Tsitologiia, vol. 24, No. 9, pp. 1080–1087, Sep. 1982.*

Izzi et al. "Fetal Liver Transplant in Aplastic Anemia and Acute Leukemia," Fetal Liver Transplantation, 237–249, 1985.*

* cited by examiner

Primary Examiner—Karen M. Hauda
(74) Attorney, Agent, or Firm—Abelman, Frayne & Schwab

(57) ABSTRACT

The invention relates to a pharmaceutical composition for the treatment of a human having acquired immune deficiency syndrome caused by HIV-infection comprising the cell suspension from either the liver, the spleen, or both, of a single human embryo.

2 Claims, 7 Drawing Sheets

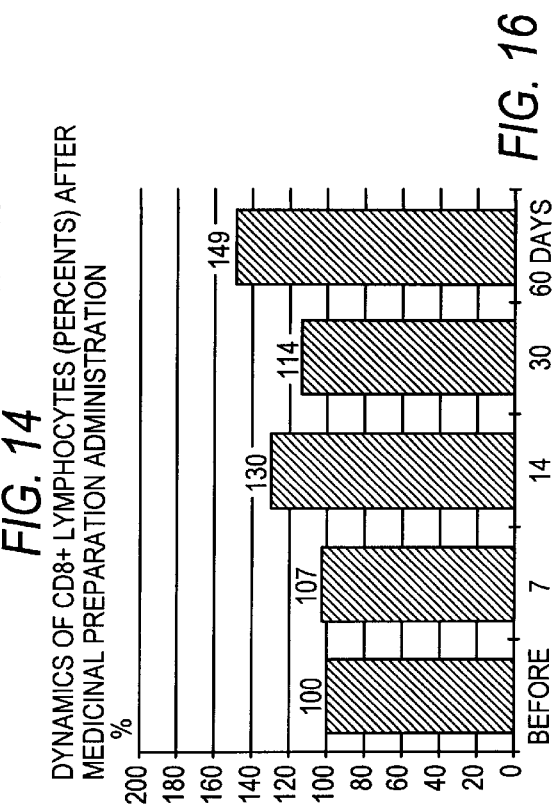
FIG. 14
FIG. 16
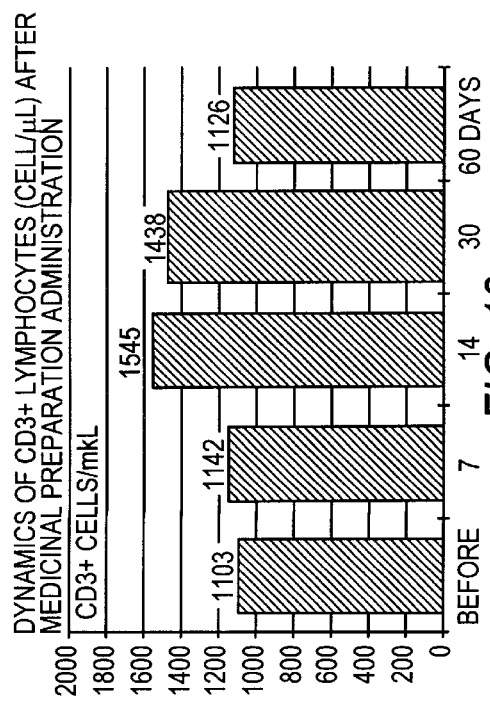
FIG. 13
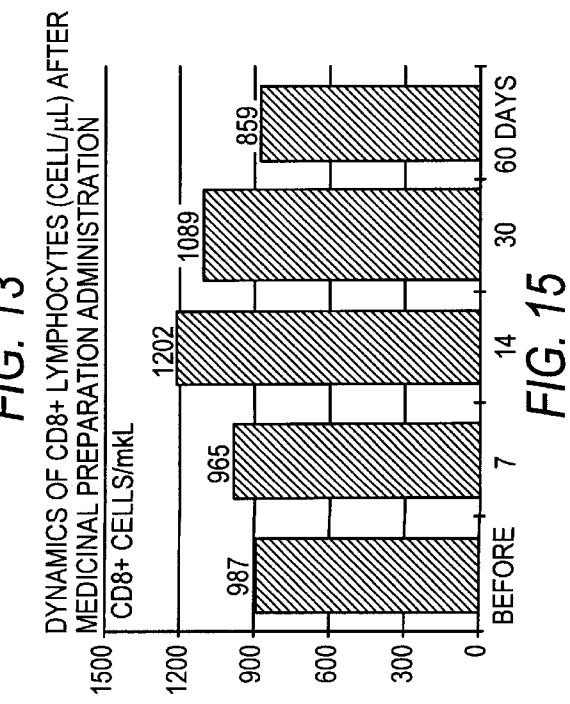
FIG. 15

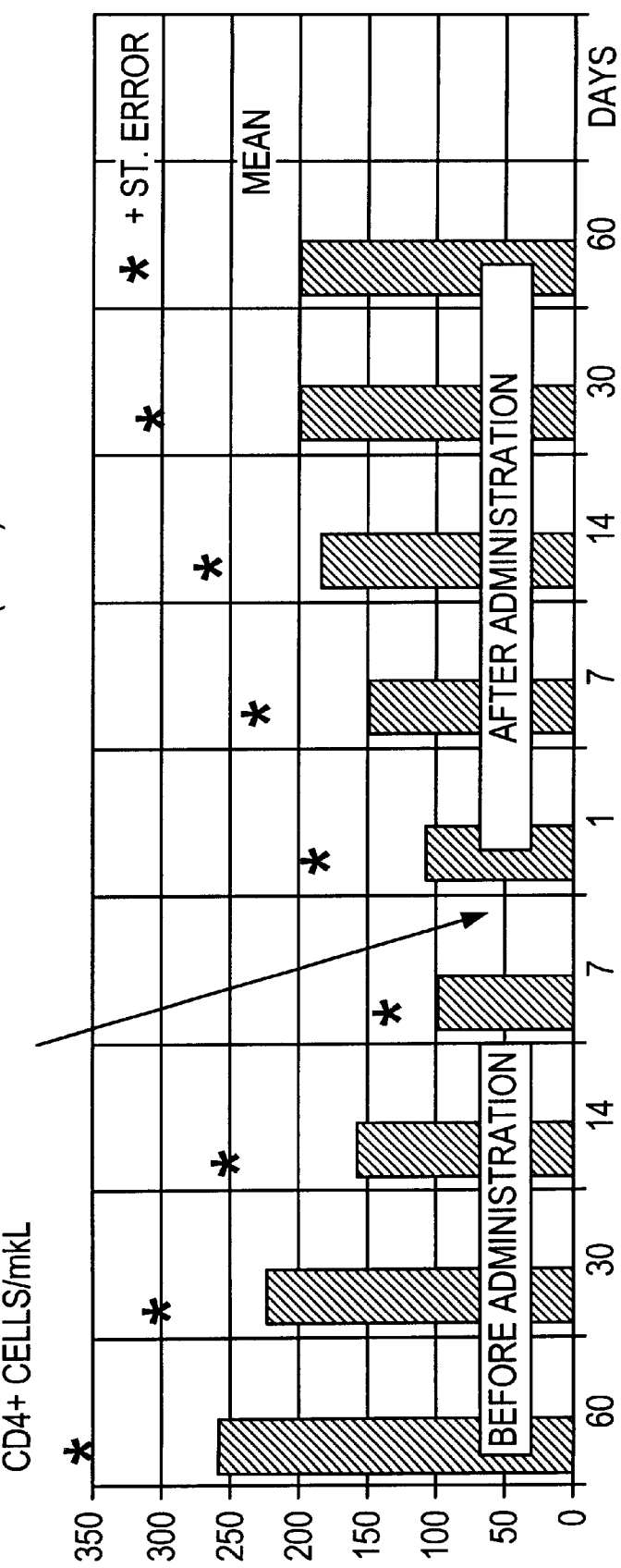

MEDICINAL PREPARATION BASED ON FETAL CELL SUSPENSION HAVING IMMUNE SUBSTITUTING EFFECT FOR PATIENTS WITH ACQUIRED IMMUNE DEFICIENCY SYNDROME (HIV INFECTION)

This application is a continuation in part of U.S. application Ser. No. 08/505,236 filed Aug. 9, 1995 and issued as U.S. Pat. No. 5,811,089.

FIELD OF THE INVENTION

This invention relates, generally, to medicine, and particularly to cell therapy, and can be applied for treating diseases caused by metabolism, hemopoietic, immunity disorders e.g. AIDS (HIV-infection).

BACKGROUND OF THE INVENTION

In recent years, a striking progress has taken place in the studies and application of human fetal cadaver tissues. A completely new area of therapy is being developed, i.e. cell therapy that permits to fill an insufficient functional activity of damaged and sore tissues through the application of medicinal preparations based on fetal cell suspensions and prepared from fetal tissues. By using cell suspensions prepared from fetal embryo tissues, it is possible to attain such conditions where embryo cells administered to the organism of a patient may survive, locate their respective target organs and produce descendants, thereby filling deficient functional units of organs and tissues.

Embryo cells are often capable of migrating, establishing intercellular links, proliferating, differentiating, and responding to effects. They can produce considerable amounts of biologically active substances, e.g. hemopoietic growth factors, interleukins, nerve growth factor, allogenic and neurotrophic factors etc. Embryo cells cause a weaker immune response than mature cells due to the late expression of the main antigens in the process of their maturation. Embryo cell suspensions contain much lower amounts of highly active cells such as leukocytes, endothelium of vessels, dendritic cells etc. During the early fetal period transplants do not have mature lymphocytes, and are tolerant to recipient's tissues.

The vital potential of various Fetal Cells and Tissues generate curative effects. Main of these effects are: recovery the suppressed hematopoiesis (normalization of the quantity of erythrocytes, leukocytes, lymphocytes, thrombocytes); stimulation, correction or suppression of the immune system; normalization of homeostasis (glycemia, lipidemia, creatinemia, mineral and water metabolism, blood pressure etc.); stimulation of trophic functions.

We believed that the most expedient way of initiation our effort would comprise a model of AIDS in which various kinds of injuries to numerous systems of the human organism are manifested. In addition, penetrating of the U.S. medical market by medicinal preparation based on Fetal Cells would be the most prospective under the flag of treatment of AIDS which constitutes s considerable menace to the U.S. society and requires urgent actions aimed at saving a great number of people suffering from this disease.

We studied the impact produced by Petal Cells and revealed their powerful curative effect on various functions of organism in patients suffering from AIDS. The methods of AIDS treatment with the use of Fetal Cells, invented by the author and contributors, has been protected by U.S. Pat. No 5,811,069 [14].

However, the about mentioned application addressed not only a method of treatment but also a medicinal preparation that would combine all the advantages related to the use of living cells with convenient way of handling, intrinsic in common medicinal preparation. We managed to prepare such preparations comprising the subject of this invention. During several years we have been using it successfully in our specialized Clinic of Cell Therapy of the National Medical University, as well as in process of providing assistance to severely sick people in medical institutions of 15 reputable research institutes and specialized centers of the Academy of Medical Science and the Ministry of public health of Ukraine in an area of treatment of numerous diseases characterized by injuries to the immune system, metabolism, and hemopoiesis. Substantiation of application of this medicinal preparation and relevant clinical examples are given hereinafter with reference to patients suffering from AIDS, wherein the inventive medicinal preparation has demonstrated its curative potential to the highest extent in case of availability of an aggravated state of numerous vital systems of the human organism.

It is a well-known fact the the destructive effect of the immune deficiency virus on the immune system starts immediately upon the moment of infection. Sensitivity to antiretroviral preparations, resistance, and capability of damaging cells are very variable among virus isolates. Numerous research workers are skeptical about the possibility of HIV elimination by using only antiretroviral preparations, probably except a short time period immediately after infection. Even if preparations result in a substantial reduction of the viral loading, the amount of lymphocyte helpers seldom comes back to the normal level. On the contrary, it usually remains over a plateau of 100 to 150/mm$^3$. In addition, there may be grave and unforeseen consequences of the long-term usage of antiretroviral therapy, which fact requires effort aimed at development of "natural", immunity-based control of HIV infection.

Although numerous studies are carried out/aimed at support and restoration of immune competence with the use of immune modulators, cytokins, growth factors, and specific immune intervention (passive immunization and vaccination), no licensed preparations are available that could restore and support immune system functions.

The progress of AIDS involves two sides:
infection with HIV, its reproduction inside organism, and attack on patient's immune system, and
increase in the activity of immune response of patient's organism, aimed at neutralizing the HIV attack, exhaustion of the functional activity of the immune system, and subsequent decrease in the production of important components of the immune system as a result of exhaustion of the leukocytic branch of hemopoiesis.

Therefore, treatment of the disease is directed at both sides of the process:
suppression of HIV reproduction with the use of antiretroviral preparations, and
strengthening (in HIV-infected and carriers) and restoration (in AIDS patients) of the functional activity of immune system, and compensation of insufficient own immune response.

At present, much success has been achieved in the suppression of HIV replication. As you know, however, this does not result in the recovery of patients suffering from AIDS and HIV-infection.

Restoration of the functional activity of immune system constitutes an independent task in the course of treatment of patients suffering from AIDS and HIV-infection.

We suppose that the most success will be attained through combination of using antiviral therapeutic means aimed at suppression of virus replication, and the inventive medicinal preparation directed at restoration of the functional activity of the patient's immune system.

In recent years, a striking progress has taken place in the studies and application of human fetal cadaver tissues. A completely new area of therapy is being developed, i.e. cell therapy that permits to fill an insufficient functional activity of damaged and sore tissues through the application of medicinal preparations based on fetal medicinal preparation and prepared from fetal tissues.

By using medicinal preparation prepared from fetal embryo tissues, it is possible to attain such conditions where embryo cells administered to the organism of a patient may survive, locate their respective target organs and produce descendants, thereby filling deficient functional units of organs and tissues.

Embryo cells are often capable of migrating, establishing intercellular links, proliferating, differentiating, and responding to effects. They can produce considerable amounts of biologically active substances, e.g. hemopoictic growth factors, interleukins, nerve growth factor, allogenic and neurotrophic factors etc.

Embryo cells cause a weaker immune response than mature cells due to the late expression of the main antigens in the process of their maturation. Embryo cell suspensions contain much lower amounts of highly active cells such as leukocytes, endothelium of vessels, dendritic cells etc. During the early fetal period transplants do not have mature lymphocytes, and are tolerant to recipient's tissues.

Embryo cell suspensions possess higher resistance than mature cells, they are capable of surviving under lower levels of oxygen contents. Since they do not have either long processes or strong intercellular adhesion, such cells are less susceptible to traumatic damage during suspension preparation. Finally, they pass the conditions of programmed cryofreezing and unfreezing in an easier and simpler way, while maintaining all of their amazing properties and being less damaged than mature cells.

At present, applied are suspensions prepared from fetal brain, bone marrow, liver, spleen, thymus, pancreas, and culocutaneous graft.

The most successful initial attempts to apply cell suspensions involved human fetal liver and spleen.

Embryo cell suspension prepared from liver and not subjected to selection and cell grading comprises a complicated concentrated multifunctional suspension consisting of a liquid, biologically active substances and cells that are changing in a very dynamic way, depending on embryo's age.

In 1973, suspension of native cells of a fetal liver of a 7-week gestation was prepared for the first time; administration of this suspension resulted in the recovery of hemopoiesis in a patient suffering from aplastic anemia (Kelemen E. Second J. Gematol., 1973, v. 10, No.4, pp.305–308 [6]).

In recent years, by varying methods of preparing of transplantat and procedures of their application, research workers managed to achieve positive results of treating primary and secondary myelodepressive states. These preparations have been described in particular in [8, 9].

An excellent paper presented by Baechelta R. et al in I. Clin. Invest., 1993, v.91, March, pp.1067–1078 [1], shows end results of treating patients suffering from grave combined immune deficiency; here, not only immunity indices have been recovered in patients, but also availability of split chimerism and emergence of tolerance to both host and donor antigens have been demonstrated.

Another area of clinical application of fetal liver cell suspension administration comprised treatment of immunity disorders and inborn errors of metabolism; here, the most considerable experience has been accumulated by Touraine J. [11–13]. J. L. Touraine is using Fetal liver transplantation. The material was taken directly from one or several fetus corps. The only characteristic of administered material comprised the amount of administered cells. J. L. Touraine did not use any special characteristics of the administered material other than identification, in some cases, of histocompatibility antigens.

It is also clear from the paper by T. Izzi and contributors from the J. Lucarelli clinic [9], that preparation of the Fetal Liver transplant took place several hours before transplantation. Transplantats characterize of high amount of cells ($10^{**}9$).

T. Izzi et al. always select material and recipient in compliance with histocompatibility antigens, which imposes a considerable restriction on their procedure.

Referring to publications by the authors working in the area of fetal liver transplantation, particularly J. Lucarelli, Touraine J. L., and others, it should be noted that they achieved much success in the treatment of patients by working within the constraints intrinsic in transplantation methods, namely:

the material that is available for transplantation in a specific situation is often non optimal for a certain patient, which fact results in selection of a recipient for the material rather than selection of a medicine for the particular patient as it is in most cases;

the use of a transplantation material ex tempore does not ensure sufficient infection safety of the treatment process;

transplantation requires selection of material in compliance with histocompatibility systems H suppression of an immune conflict between recipient and transplant;

the total amount of cells frequently comprises the only feature of a material to be transplanted;

in many cases, cell transplantation material is wasted, and cell suspensions are prepared from organs of several embryos The main object of the invention.

The object of the invention comprised development of a medicinal preparation (agent) that would combine substantial advantages of transplantation methods, and particularly would ensure transplantation of living cells having a capability to survive, reproduce and specialize inside patient's body, and advantages provided by application of medicinal preparations, and in particular would ensure convenient, safe and repeated application without patient's conditioning, and selection of a transplant for a patient (patient for transplant) in compliance with histocompatibility genes.

Full description of the acting source of the inventive medicinal preparation, taking into account its polypotent properties, polymorphous organization, features of evolution inside the organism in the course of specific differentiation, reproduction and life cycle and with account of disease specific nature and stage, is considered to be quite impossible at the modern level of knowledge, not to speak about qualitative assessment.

The inventive medicinal preparation should possess the following major advantages over the transplantation technology utilizing living cells:

increase in the concentration of nondifferentiated lymphoid elements, including progenitor cells, guaranteed preservation of their viability and capability of producing cell posterity in the patient's organism, application of the preparation without any risk of infecting a patient with infectious diseases, absence of need to select patients on the basis of major systems of histocompatibility genes, absence of need to carry out conditioning prior to treatment, absence of need to use immune depressants, absence of "host-transplant" immune conflict and rejection reaction, application immediately upon clinical prescription, repeated and multiple treatment sessions with the use of the inventive method of treatment and inventive medicinal preparations, application, in the on-going treatment course, of the same fetal material that has been already used for this patient, economical use of fetal material in fractional doses during patient's life as the clinical need arises, unlimited storage term, transportation to substantial distances.

A fuller understanding of the nature of the invention will be had from the following detailed description of embodiments thereof, taken in conjunction with specific Examples.

DESCRIPTION OF THE BEST EMBODIMENT

The medicinal preparation of the invention can be produced by using the following procedure:

Embryos are obtained after artificial abortions in healthy women who have been examined with respect to the absence of viral and hemic infections. Prenatal diagnostics include tests for syphilis, HIV-infection, VHB and VHC, toxoplasmosis, cytomegaloviral infection.

Embryos from 5–12 weeks of age are used. Vacuum extraction method of abortion is preferable from the standpoint of maintaining the integrity of a fetus.

The embryo is then transferred to a sterile vessel containing Hanks's solution and an antibiotic (group of aminoglycosides).

Hanks' solution (Hanks, Wallace, 1949) was used as a medium for the preparation of cell suspension. This balanced solution is conventionally used for the preparation of nutritive media.

| | |
|---|---|
| NaCl | 8.0 g |
| KCl | 0.4 g |
| $CaCl_2$ | 0.14 g |
| $MgCl_2$ | 0.1 g |
| $MgSO_4 * 7H_2O$ | 0.1 g |
| $Na_2HPO_4$ | 0.06 g |
| $KH_2PO_4$ | 0.06 g |
| $NaHCO_3$ | 0.07 g |
| Glucose | 1.00 g |
| Phenol (water-soluble form) | 0.02 g |

(double distilled water is stilled in glass up to 1 liter).

Calcium chloride ($CaCl_2$) is first dissolved in 30–50 ml of water, and then slowly added to the solution of other salines. If this saline is available with a high amount of crystallized water ($Na_2HPO_4*12H_2O$), then 2 g of saline are added. The resulting solution is filtered through a paper or cotton-gauze filter. Following this, the solution is poured into glass dishes and corked with cotton-gauze stoppers; it is then sterilized by streaming vapor at 100° C., without tension, for 20 minutes, 3 days one after another.

Upon adding phenol red indicator, the solution becomes orange-red. To determine pH value, sterile 1.4% solution of sodium bicarbonate ($NaHCO_3$) is added to Hanks' solution. To carry out work with a culture, pH value of Hanks' solution must be within 7.2–7.4.

Hanks' solution that does not contain any phenol red is used for adding to the cell suspension upon homogenization.

It is stored at 4–6° C.; room temperature is also possible. Expiration term is 1 month. Subsequent work is carried out under sterile conditions of a laminar box. Embryos are transferred to sterile Petri dishes filled with Hanks's solution and antibiotic; here, after the abdominal cavity has been carefully opened, liver and spleen are extracted and used separately to prepare suspensions.

The organs are placed into homogenizers, cut into small fragments and ground to prepare a homogeneous mass. Fetal cell suspensions prepared from liver and have not been subjected to selection and cell grading, comprise a complicated and concentrated multifunctional suspension that consists of cells (about 70 vol %), fluid (about 30 vol %), biologically active substances and other macromolecules, organic and inorganic ions. The volume of produced suspension is 0.5 to 2.5 ml/ the amount of nucleated cells being about $10^9$. Cells are washed down, with Hanks's solution, from homogenizer walls and pestle and into graduated test tubes, while passing them first through the filter used for transfusion of blood preparations, and then through diminishing-diameter needles. Portions of the thus prepared suspension are transferred to plastic containers and closed hermetically.

These portions will be subjected to cryopreservation.

Cryopreyervation of medicinal preparation

Upon preparation of medicinal preparation, including addition of cryprotector, resulting medicinal preparation are poured into containers with threaded stoppers, each having 2 ml capacity. Each container is filled with suspension in an amount of 0.5 to 2 ml. Dimethylsulfoxide (DMSO, chemically pure) is used as a cryoprotector. DMSO comprises a well-known cryoprotector. Prior to its use, DMSO is passed through a millipore filter (pore diameter of 0.22 $\mu$m).

With light stirring, the cell suspension it is added, prior to cryopreservation thereof, with drops of fresh working solution of DMSO whose amount is equal to that of the cell suspension (1.4 mole/liter). Final concentration of DMSO in resulting cell suspension amounts to 3–10%. No washing of the preparation to remove DMSO prior to treatment is required. During its dilution in the isotonic solution of sodium chloride, prior to be administered to a recipient, this concentration accordingly decreases by 50 to 100 times; therefore, the resulting substance is not toxic for human organism.

Moreover, DMSO acts as a conductor of biologically active substances through biological barriers and membranes, thereby promoting the biologic effect of treatment. Addition of specified doses of this cryoprotector to the inventive preparation permits to attain an additional positive effect associated with overcoming violations of barrier functions of vessels. Being a conductor of biologically active substances in tissues, DMSO improves the efficiency of action of the inventive preparation.

The resulting cell suspension may be tested according to the following parameters total amount (contents) of nucleated cells in 1 ml (cell analyzer or visually, under microscope, in a counting chamber);

Colony-forming units of the granulocyte/macrophage (CFU GM) 1 ml by methods of CFU cloning in methyl cellulose [4];

Colony-forming units of the granulocyte, erythrocyte, monocyte/macrophage, megakaryocyte (CFU GEMM)" in 1 ml [4];

Progenitor cells (CD34). CD34 in 1 ml (by indirect immunofluorescent test with the panel of monoclonal antibodies).

Prior to cryopreservation, the composition of the fetal suspension was described as follows:
   a) the contents of nucleated cells is 8 to 360'10$^6$/ml;
   b) the contents of colony-forming units of granulocyte/macrophage is 10 to 260'10$^3$/ml;
   c) the contents of colony-forming units of granulocyte, erythrocyte, monocytelmacrophage, megakaryocyte is 0.5 to 30'10$^3$/ml; and
   d) the contents of progenitor cells (CD34) is 1 to 12'10$^6$/ml.

Cell composition is represented by the following cell types

| | |
|---|---|
| Cells of erythroid and megaloblastic series (erythroblasts, basophilic, polychromatophilic and oxyphilic normocytes, megaloblasts and megalocytes) | 74.5 ± 5.8% |
| Cells of lymphoid series (lymphocytes, lymphoblasts, undifferentiated blasts) | 3.5 ± 1.7% |
| Cells of myeloid series (myeloblasts, myelocytes, granulocytes, monoblasts, monocytes) | 2.0 ± 1.6% |
| Hepatocytes | 16.5 ± 4.2% |
| Other cells (megacariocytes, fibroblasts, epithelial cells, adipocytes, nuclei) | 3.0 ± 0.7% |

Cell suspension of each embryo is always provided with 6 control containers having the following purpose:

1 container with 0.5 ml of cell suspension is intended for testing the functional validity of cell suspension upon unfreezing;

3 containers with 1.0 to 1.5 ml of cell suspension each are intended for viral control of the given embryo. For these containers, cell suspension is prepared from culocutaneous graft of the same embryo, similarly to preparation of cell suspension from liver and spleen. One container is studied for virus infections in the laboratory of cell suspension producer, while another container is handed over for parallel study in a public supervisory laboratory. The third container remains permanently at the cryogenic storage facility, for the purpose of further confirmation of material safety, including viral and bacterial ones). The material for which viruses are detected even in one container, is destroyed by burning together with all the remaining amount prepared from the same embryo.

2 containers with 1.0 to 1.5 ml each of rinse water from laboratory ware and instruments are intended for studies of bacterial sterility. Container 1 is studied in the producer's laboratory, and container 2, in the state supervisory laboratory.

All the containers except 2 intended for viral control and 2 intended for bacterial testing are subject to programmable cryogenic freezing down to −196° C. Containers are placed in vertical position into the chamber of programmable cryogenic freezing device. Freezing is carried out in 3 stages [2]:
   stage 1: from room temperature down to −4° C., at a rate of 1° C./min;
   stage 2: from −4 down to −10° C., at a rate of 0.1° C./min;
   stage 3: from −10° C. down to −190° C., at a rate of 7° C./min.

Following this, containers are transferred to biological safes where they are stored in liquid nitrogen for unlimited period of time till application.

Unfreezing of medicinal preparation

Unfreezing of medicinal preparation is carried out directly before their application. Unfreezing program comprises two phases, fast and slow ones.

Material passes the fast unfreezing phase by means of placing the container into water bath at 40° C. (overheating above 42° C. is impermissible), till occurrence of a small movable piece of ice in the center of container.

This is followed by slow phase at room temperature, till disappearance of the above piece of ice in the container that has been removed from water bath.

Unfrozen cell suspension can be stored at room temperature for not more than 2 hours.

Testing of functional condition of cryopreyerved Medicinal preparation

Upon preparation of a Medicinal preparation and its cryopreservation, the control container holding 0.5 ml of cell suspension is used for testing the functional condition of material. To this end, this container is unfrozen in compliance with a program that is used to unfreeze all the remaining containers.

In the unfrozen portion of cell suspension, conventional methods, as mentioned above, are used to identify:
   total amount (contents) of nucleated cells in 1 ml (cell analyzer or visually, under microscope, in a counting chamber);
   Colony-forming units of the granulocyte/macrophage (CFU GM) 1 ml by methods of CFU cloning in methyl cellulose;
   Colony-forming units of the granulocyte, erythrocyte, monocyte/macrophage, megakaryocyte (CFU GEMM)" in 1 ml;
   Progenitor cells (CD34). CD34 in 1 ml (by indirect immunofluorescent test with the panel of monoclonal antibodies).

Following this, used and stored in the tissue bank are medicinal preparation having the following parameters:
   a) the contents of nucleated cells is 5 to 200'10$^6$/ml;
   b) the contents of colony-forming units of granulocyte/macrophage is 20 to 200'10$^3$/ml;
   c) the contents of colony-forming units of granulocyte, erythrocyte, monocyte/macrophage, megakaryocyte is 0.5 to 50'10$^3$/ml; and
   d) the contents of progenitor cells (CD34) is 1 to 20'10$^6$/ml.

Cell composition is represented by the following cell types

| | |
|---|---|
| Cells of erythroid and megaloblastic series (erythroblasts, basophilic, polychromatophilic and oxyphilic normocytes, megaloblasts and megalocytes) | 78.4 ± 4.2% |
| Cells of lymphoid series (lymphocytes, lymphoblasts, undifferentiated blasts) | 8.5 ± 5.4% |
| Cells of myeloid series (myeloblasts, myelocytes, granulocytes, monoblasts, monocytes) | He opene-IROTCR |
| Hepatocytes | 3.5 ± 2.2% |
| Other cells (mainly nuclei) | 8.5 ± 5.9% |

Prenatal diagnostics include tests for syphilis, HIV-infection, VHB and VHC, toxoplasmosis, cytomegaloviral infection. Container contents sterility tests are performed.

Fetal diagnostics include tests for HIV-infection, VHB and VHC, cytomegalovirus, rubella virus, herpes and toxoplasmosis.

Repeated diagnostics of availability of HIV-infection in a donor is carried out 90 to 100 days after abortion.

The mode of administration of Medicinal preparation to recipient's body in the process of treatment.

Medicinal preparation prepared from fetal liver and/or spleen are most preferably administered intravenously as demonstrated in Examples, although also possible are such modes as intra-abdominal or intraosteal. Given below are possible specific procedures of such administration.

Medicinal preparation can be administered intravenously, in drops, in the composition of 100–150 ml of isotonic solution of sodium chloride, at a rate of 20 to 40 drops a minute.

With intra-abdominal administration, the cell suspension is diluted with isotonic solution of sodium chloride up to a total amount of 50 ml, and administered intra-abdominally, in the form of a jet.

In case where a patient has a fresh thrombus or hemophthalmopathy (hemorrhage in eye tissues), as well in cases of hypersplenism, it is expedient to use intraosteal administration of cell suspension in the chest, in an amount of up to 50 ml of isotonic solution of sodium chloride, and in the form of a jet.

The amount of administered preparation may go up to whole amount of medicinal preparation prepared from liver and spleen of one human embryo that usually does not exceed approximately 10.0 ml. Here, the quantity of utilized 2-ml containers with the preparation may vary preferably from 1 to 16. Generally, the amount of cell suspension administered during one treatment session ranges within 0.5 to 2.0 ml (1 to 3 containers).

Also possible is a combined use of medicinal preparation prepared from fetal liver and fetal spleen.

Repeated administration of preparation

In case of repeated administration of the medicinal preparation during subsequent stages of patient's treatment, preferred is application of the Medicinal preparation prepared from the same embryo that was previously used. To implement this feature of the method of preparation of Medicinal preparation from a fetal organ, such Medicinal preparation is distributed to several containers. Medicinal preparation is assigned to a specific patient and stored in the cryobank for future use with the same patient.

To authors' opinion, an advantage of the inventive method comprises the possibility of attaining full-scale therapeutic effect through application of small doses of the fetal material.

Medicinal form

Fluid containing cells, biologically active substances, electrolytes, DMSO.

Scientific substantiation

Medicinal preparation was received by 63 patients suffering from HIV-disease and staying at the AIDS Department of the L. V. Gromashevski Kyiv Research Institute for Epidemiology and Infectious Diseases, Department of Infectious Diseases of the Zaliznychni District Clinical Hospital No.4 (Kyiv), Odessa Oblast Center for AIDS Prevention and Control, EmCell Center of Cell Therapy and O. O. Bogomolets National Medical University.

When drawing patients to studies, we adhered to the international ethical requirements developed in 1982 by the International Council of Medical Societies and WHO (Provisional International Ethical Requirements for Biomedical Studies Involving Humans). In case of treatment with the use of the Medicinal preparation, patient's consent was received in every instant. In 50% cases, patients themselves requested application of the Medicinal preparation. A patient received all the necessary information on treatment procedure, anticipated positive results, and possible risk. Each patient had the right to refuse from further treatment or any kind of manipulations at any stage of studies; in such case, he/she received no refusal to restore treatment upon his\her subsequent request. Any patient was provided with confidentiality of the contents of entries made in the protocols; besides, identification of personality was made impossible without patient's consent. In each case, the treatment was agreed upon with a physician upon discussing treatment objective, procedure and anticipated results, as well as duration of participation in the studies. Any possibility of pressure exerted by physician upon participants of studies was eliminated.

Patients did not receive money or any kind of compensation for their participation in the studies; therefore, they did not have any additional motivation for such participation except consideration of treatment usefulness for their own health. They received additional medical care under common grounds. The main group consisted of 38 patients for which preliminary selection criteria had been developed: impossibility of using antiviral therapy because of intolerance or considerable side effects; more than 50% decrease in CD4+ during preceding 6 months or 100/1 $mm^3$ reduction during the same time; progress of disease from ARC (AIDS-related complex) to AIDS; worsening of capacity for work and quality of living (decrease in Karnofsky [5]index by more than 20% during last 6 months); actual incurability of a patient (CD4+ amount less than 50/$mm^3$ in manifestation of AIDS-indicator diseases, and with Karnofsky index value below 30%). Average age of patients was 36 years (within 23 to 54 years); average time since the date of detection of the fact of infection, 5 years; average level of CD4+ lymphocytes, 183/$mm^3$. The control group comprised 25 patients that had a stable progress of disease during last 6 months and were not subjected to antiviral therapy. Average age was 35 years (within 25 to 39 years); average time since the date of detection of the fact of infection, 5 years; average level of CD4+ lymphocytes, 385/$mm^3$. Majority of patients participating in the studies were males (51 per 12 females) suffering from ARC since this phase of disease is the most prospective for supporting therapy.

Most frequently immune deficiency was manifested through oral candidiasis, diarrhea and herpes (Table 1.1).

TABLE 1

Diseases - indicators of immunodeficiency in patients of main and control groups

| Diseases - indicators of immunodeficiency | All investigated group of patients N = 63 | | Group, treated with Med. Prep. N = 38 | | Control group N = 23 | |
|---|---|---|---|---|---|---|
| | abs | % | abs | % | abs | % |
| Diarrhea > 1 month | 23 | 36.5 | 14 | 22.2 | 9 | 14.3 |
| Oral candidosis | 19 | 30.2 | 14 | 22.2 | 5 | 7.9 |
| Persistent Lymphoadenopathy | 15 | 23.8 | 1 | 1.5 | 14 | 22.2 |
| Herpes vulgar | 13 | 20.6 | 11 | 17.5 | 2 | 3.2 |

TABLE 1-continued

Diseases - indicators of immunodeficiency in patients of main and control groups

| Diseases - indicators of immunodeficiency | All investigated group of patients N = 63 | | Group, treated with Med. Prep. N = 38 | | Control group N = 23 | |
|---|---|---|---|---|---|---|
| | abs | % | abs | % | abs | % |
| Neurologic manifestations | 5 | 7.9 | 5 | | | |
| Pulmonary tuberculosis | 4 | 6.3 | 3 | 4.8 | 1 | |
| Kaposi's sarcoma | 3 | 3.2 | 1 | 1.5 | 1 | |
| Cytomegalovirus | 2 | 3.2 | 2 | 3.2 | | |
| Pneumonia | 2 | 3.2 | 2 | 3.2 | | |
| *Leukoplacia filiformis* | 1 | 1.5 | 1 | 1.5 | | |
| *Molluscum contagiosum* | 1 | 1.5 | 1 | 1.5 | | |
| Dementia | 1 | 1.5 | 1 | 1.5 | | |

Majority of patients in the group were either capable of working or could serve themselves, while minority of these patients were disabled: Karnofsky Index in 22 (57.9%) patients amounted to 100–80; Karnofsky Index in 10 (26.3%) patients was 70–50; Karnofsky Index in 6 (15.8%) patients was 40–10. In the control group, at the beginning of observation all the patients were capable of working (Karnofsky Index value of 100–80). Patients having high values of Karnofsky Index were generally ambulant; in case of reduction of this index below 80 points, they stayed at the hospital. By the time of transplantation, 20 (52.6%) patients from the group of recipients were ambulant, and 18 (47.4) patients stayed at the hospital. Immune examination was carried out in the control group at the beginning of their stay at the hospital.

The longest observation time, i.e. over 5 years, was in three patients that were observed during 12 months more after this analysis of results.

Also separated are groups of patients suffering from ARC and AIDS (according to the classification adopted by the Disease Control Center in Atlanta, 1986). The ARC group consisted of 26 patients (7 females and 19 males). Average age was 36 years (within 23 to 54). Karnofsky Index ranged within 50 to 100. Average time of observation was 12 months (between 1 and 48). Average amount of CD4+ was 233 cells/mm$^3$ (15–631). Average amount of CD3+ was 1296 cells/mm$^3$ (189–2700). Average amount of CD8+ was 1118 cells/mm$^3$ (195–2663). Average absolute amount of lymphocytes was 1936 cells/mm$^3$ (452–4028). ARC was manifested in 10 patients in the form of persisting generalized lymphadenopathy (group III); in 2 patients, by general diseases (group IV, subgroup A); in 4 patients, by neurologic disorders (group IV, subgroup B); in 3 patients, by pulmonary tuberculosis (group IV, subgroup C2); in 5 patients, by oral candidiasis (group IV, subgroup C2); in 1 patient, by Leukoplacia, and in 1 patient, by mollusk (group IV, subgroup C2).

The AIDS group comprised 8 patients (2 females and 6 males). Average age was 34 years (between 32 and 38). Karnofsky Index ranged within 10 to 90. Average time of observation was 4 months (1 to 10). Average amount of CD4+ was 43 cells/mm$^3$ (6–189). Average amount of CD3+ was 358 cells/mm$^3$ (157–679). Average amount of CD8+ was 318 cells/mm (89–610). Average absolute amount of lymphocytes was 725 cells/mm$^3$ (241–1394). AIDS was manifested in 2 patients by cytomegaloviral infection and pneumocystic pneumonia (group IV, subgroup Cl); 2 patens, Kaposi's sarcoma in 2 patients (group D), and in 4 patients, by cachexia syndrome.

Statistic of the CD4, CD3 and CD8 dynamic in AIDS patients. The graphs given below present data that evidence positive effect of administration of the medicinal preparation on indices such as CD3, CD4, and CD8.

BRIEF DESCRIPTION OF THE DRAWINGS

FIG. 13 is a graph of CD3+ lymphocytes (cell/$\mu$L) after medicinal preparation administration;

FIG. 14 is a graph of dynamics of CD3+ lymphocytes (percents) after medicinal preparation administration;

FIG. 15 is a graph of dynamics of CD8+ lymphocytes (cell/$\mu$L) after medicinal preparation administration;

FIG. 16 is a graph of dynamics of CD8+ lymphocytes (percents) after medicinal preparation administration;

FIG. 19 is a graph of dynamic of D4+ lymphocytes in AIDS patients that received antiretroviral therapy prior and after administration of medicinal preparation (N=10).

Immune Indices in AIDS Patients After Administration of Medicinal Preparation

| Indices | Normal rate(mm3) | Stat, ind. | Before 0 | After treatment (days) 7 | 12 | 30 | 60 |
|---|---|---|---|---|---|---|---|
| CD3+ | 700–2000 | M | 1261 | 1250 | 1578* | 1504* | 1258 |
|  |  | mm | 152 | 177 | 214 | 220 | 191 |
|  |  | p |  |  | 0.03 | 0.03 |  |
|  |  | n | 22 | 22 | 22 | 22 | 15 |
| CD4+ | 400–1500 | M | 226 | 240 | 330* | 265 | 338 |
|  |  | mm | 39 | 44 | 70 | 51 | 84 |
|  |  | p |  |  | 0.05 |  |  |
|  |  | n | 22 | 22 | 22 | 22 | 14 |
| CD8+ | 150–800 | M | 1064 | 1119 | 1326* | 1240 | 1091* |
|  |  | mm | 157 | 195 | 222 | 229 | 172 |
|  |  | p |  |  | 0.02 |  | 0.05 |
|  |  | n | 22 | 22 | 22 | 22 | 14 |
| CD4+/CD8+ | 0.6–2.5 | M | 0.35 | 0.44 | 0.48 | 0.44 | 0.28 |
|  |  | mm | 0.10 | 0.12 | 0.13 | 0.12 | 0.09 |
|  |  | p |  | 0.02 |  |  |  |
|  |  | n | 22 | 22 | 22 | 22 | 12 |
| CD22+ | 200–500 | M | 163 | 248 | 279* | 273* | 233 |
|  |  | mm | 56 | 90 | 90 | 88 | 64 |
|  |  | p |  |  | 0.04 | 0.04 |  |
|  |  | n | 9 | 9 | 9 | 9 | 4 |
| Lympho-cytes | 700–3600 | M | 1930 | 2220 | 2427* | 2328* | 2241 |
|  |  | mm | 214 | 276 | 304 | 297 | 319 |
|  |  | p |  |  | 0.04 | 0.03 |  |
|  |  | n | 22 | 22 | 22 | 22 | 14 |

*Significant

Out of the total amount of 20 patients for whom multiple studies of the immune status have been performed, only 3 patients (15%) did not provide any positive response to administration of the medicinal preparation. Given in Appendix are charts containing the data on 17 patients in which positive effect of CD4 was observed after administration of the medicinal preparation. Since the range of initial values of CD4 is very wide, we divided all patients into 6 groups according to the level of CD4 initial values.

Figure 1:
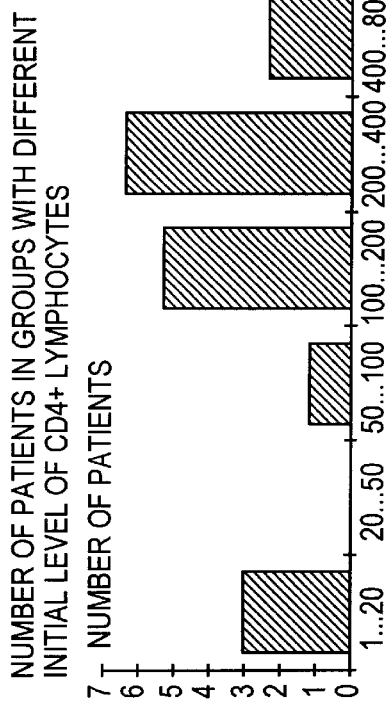
FIG. 1 is a graph depicting average initial CD4+ lymphocyte level in groups with different initial CD4+ level (Cells/$\mu$L)
Figure 2:
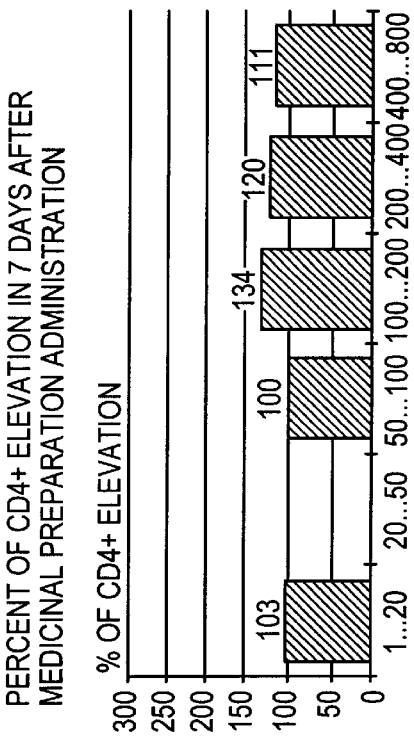
FIG. 2 is a graph of the number of patients in groups with different initial level of CD4 + lymphocytes.

FIG. 1 demonstrates average values and standard errors for CD4 in each group prior to administration of Medicinal preparation. FIG. 2 gives the number of patients in each group.

Figure 3:
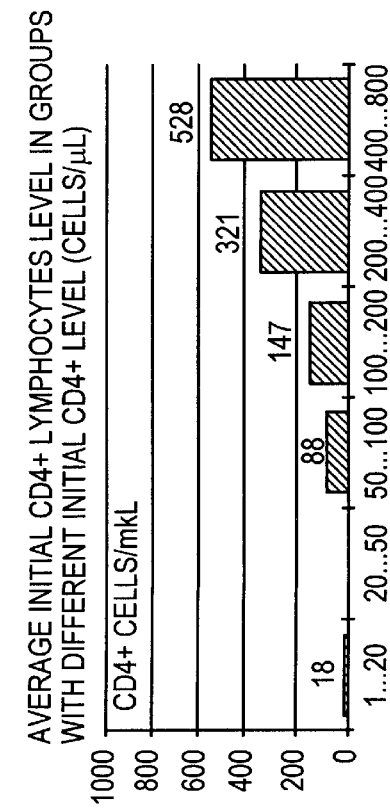
FIG. 3 is a graph of the average initial CD4+ level in groups (cells/$\mu$L) in 7 days after medicinal preparation administration.
Figure 4:
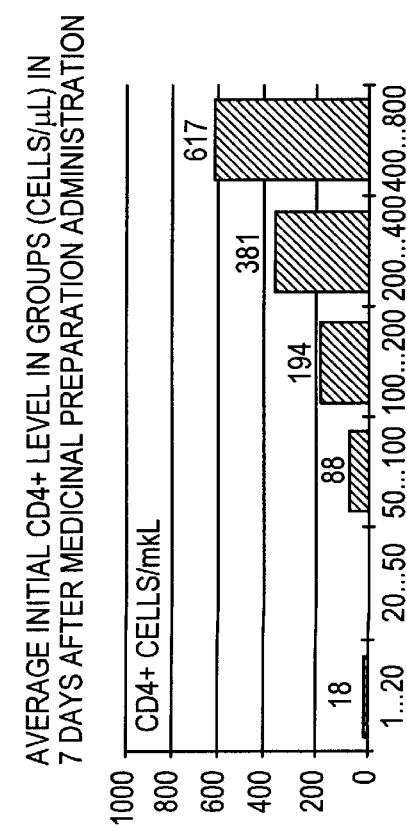
FIG. 4 is a graph of percent of CD4+ elevation in 7 days after medicinal preparation administration.
Figure 5:
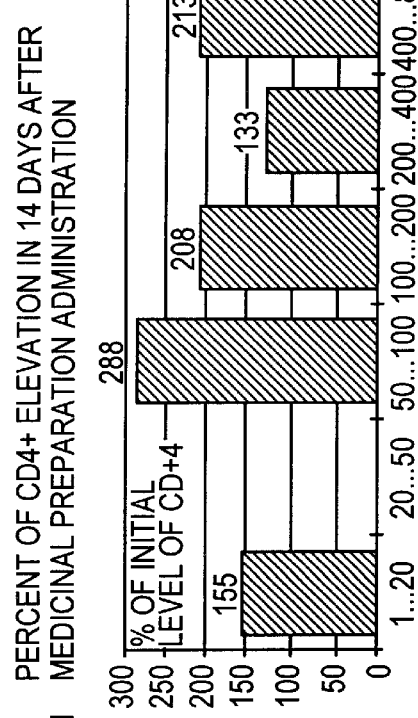
FIG. 5 is a graph of average initial CD4+ level in groups (cells/mL) in 14 days after medicinal preparation administration.
Figure 7:
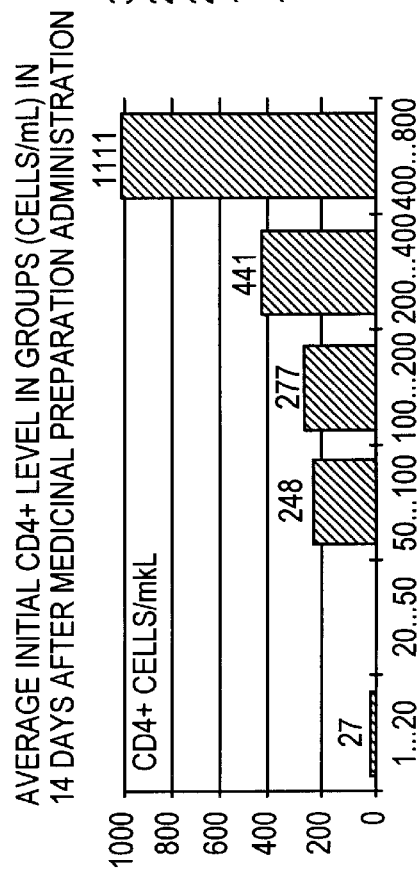
FIG. 7 is a graph of average initial CD4+ level in groups (cells/$\mu$L) in 30 days after medicinal preparation administration.
Figure 6:
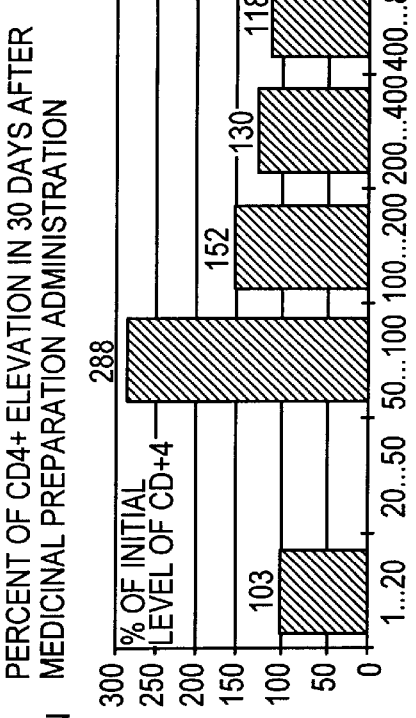
FIG. 6 is a graph of CD4+ elevation in 14 days after medicinal preparation administration.
Figure 8:
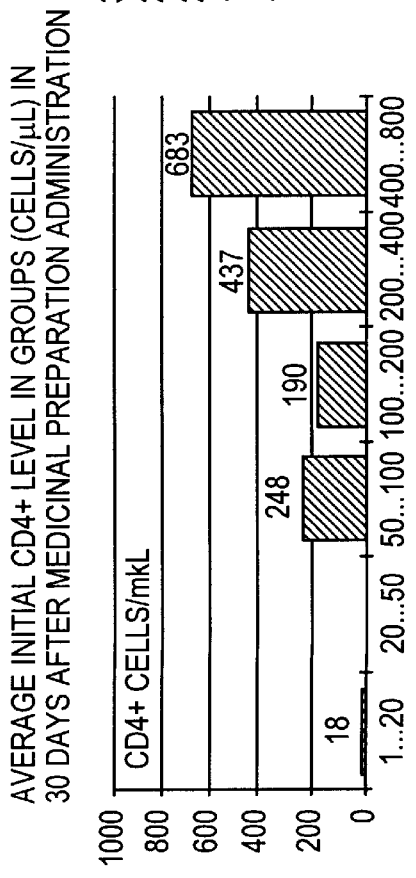
FIG. 8 is a graph of percent of CD4+ elevation in 30 days after medicinal preparation administration.
Figure 9:
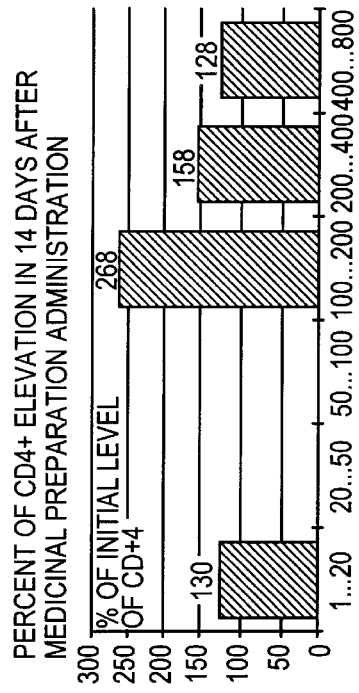
FIG. 9 is a graph of average initial CD4+ level in groups (cells/mL) in after medicinal preparation administration.
Figure 10:
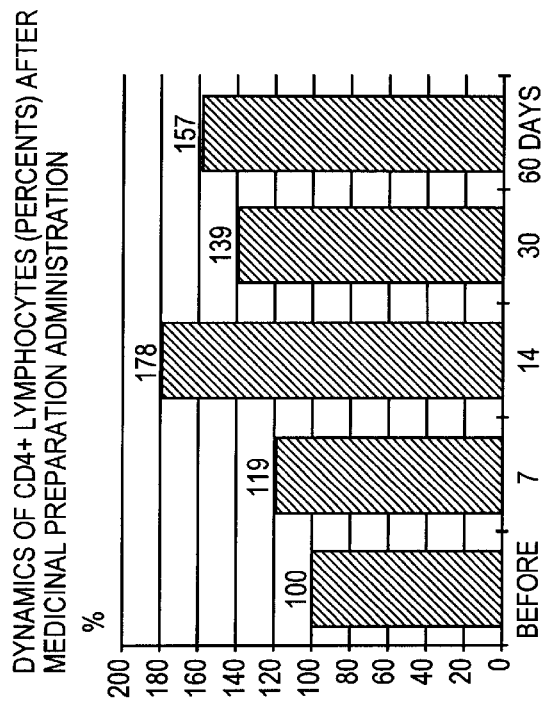
FIG. 10 is a graph of percent of CD4+ elevation in 14 days after medicinal preparation administration.

FIG. 3 shows the data on CD4 levels in relevant groups 1 week after administration of Medicinal preparation, and FIG. 4 demonstrates percentage of these values with respect to the initial level. Changes after 2 weeks are given in FIGS. 5 and 6, respectively. It can be seen that in three groups an increase in CD4 exceeds 200%. After 1 month term, when stimulating effects go and relative decrease of CD4 level is observed, 2 months after administration of Medicinal preparation a second wave of CD4 level increase is observed, associated with the immune substituting effect (FIGS. 9 and 10) (groups having CD4 levels of 1–20, 100–200, and 200–400 in $mm^3$).

Figure 11:
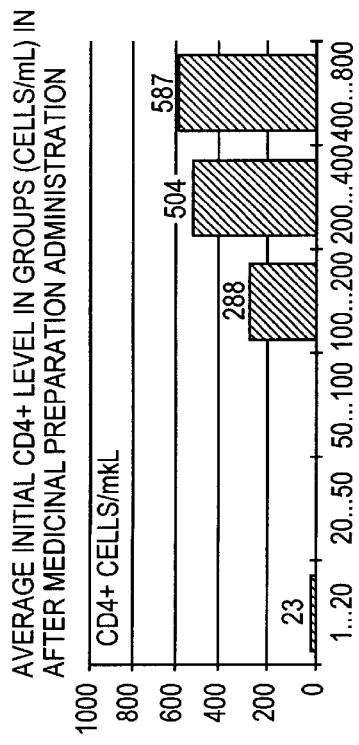
FIG. 11 is a graph of dynamics of CD4+ lymphocytes (cell/$\mu$L) after medicinal preparation administration.
Figure 12:
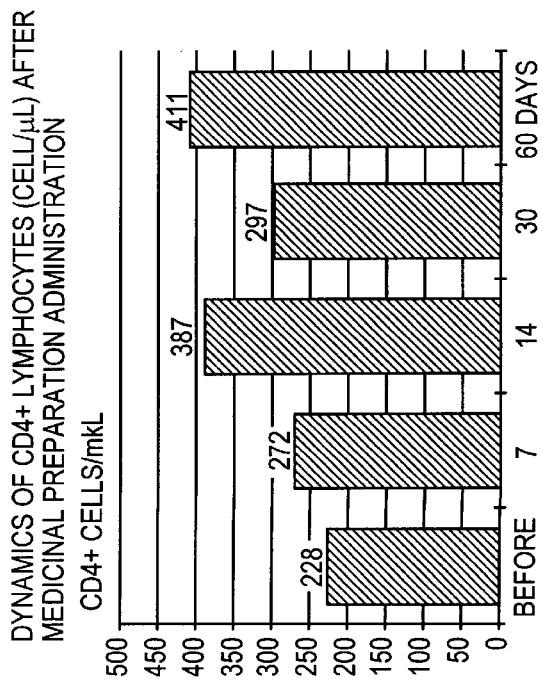
FIG. 12 is a graph of CD4+ lymphocytes (percents) after medicinal preparation administration.

In FIGS. 11 and 12, dynamics of CD4 variations is given without division into groups according to initial levels. Presented are validity levels of differences as compared to the initial value of CD4: after 1 and 2 weeks, and 2 months the increase of CD4 level is statistically valid.

Similar data on CD3 (FIGS. 13 and 14) evidence statistically valid increase of the level 2 weeks and 1 month after administration of Medicinal preparation.

The data on CD8 (FIGS. 15 and 16) evidence valid increase 2 weeks and 2 months after administration of Medicinal preparation.

Figure 17:
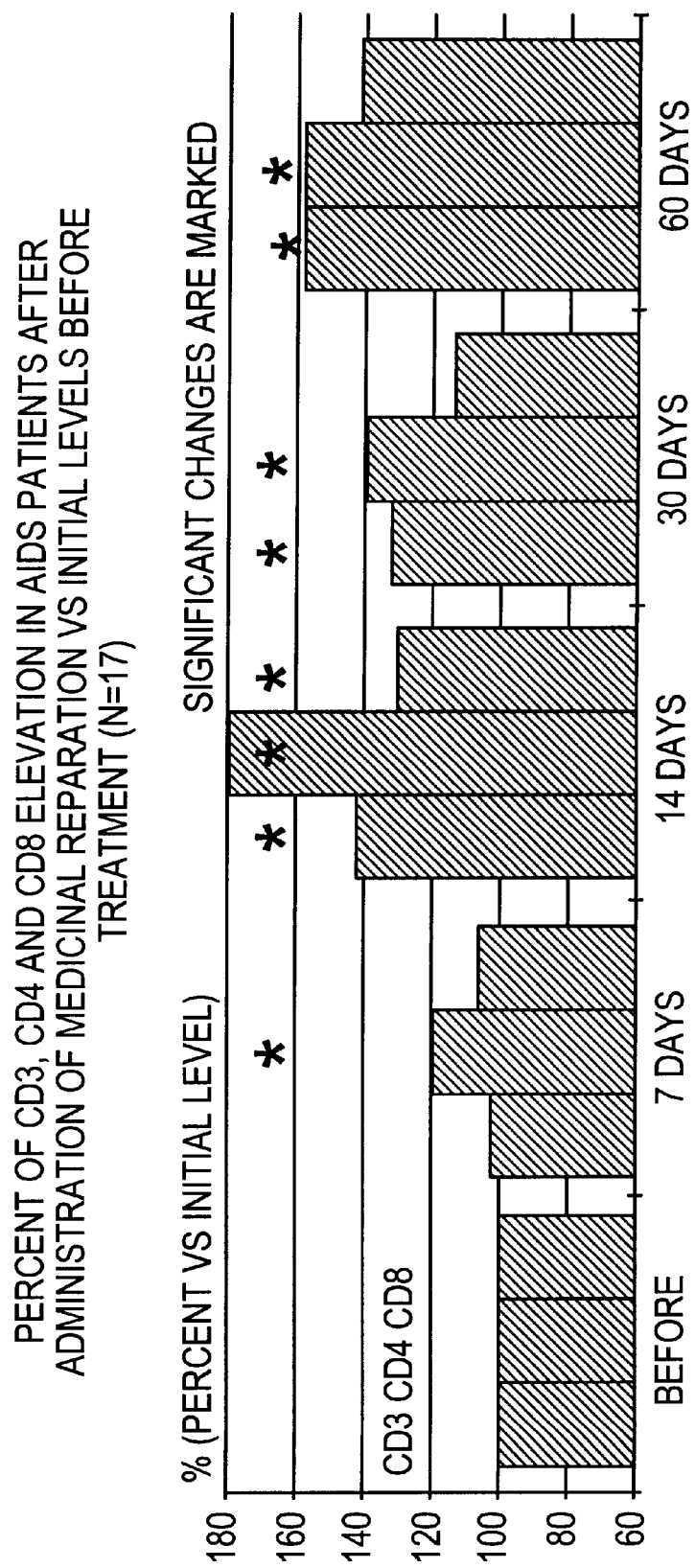
FIG. 17 is a graph of percent of CD3, CD4 and CD8 elevation in AIDS patients after administration of medicinal preparation vs. initial levels before treatment (N=17)
Figure 18:
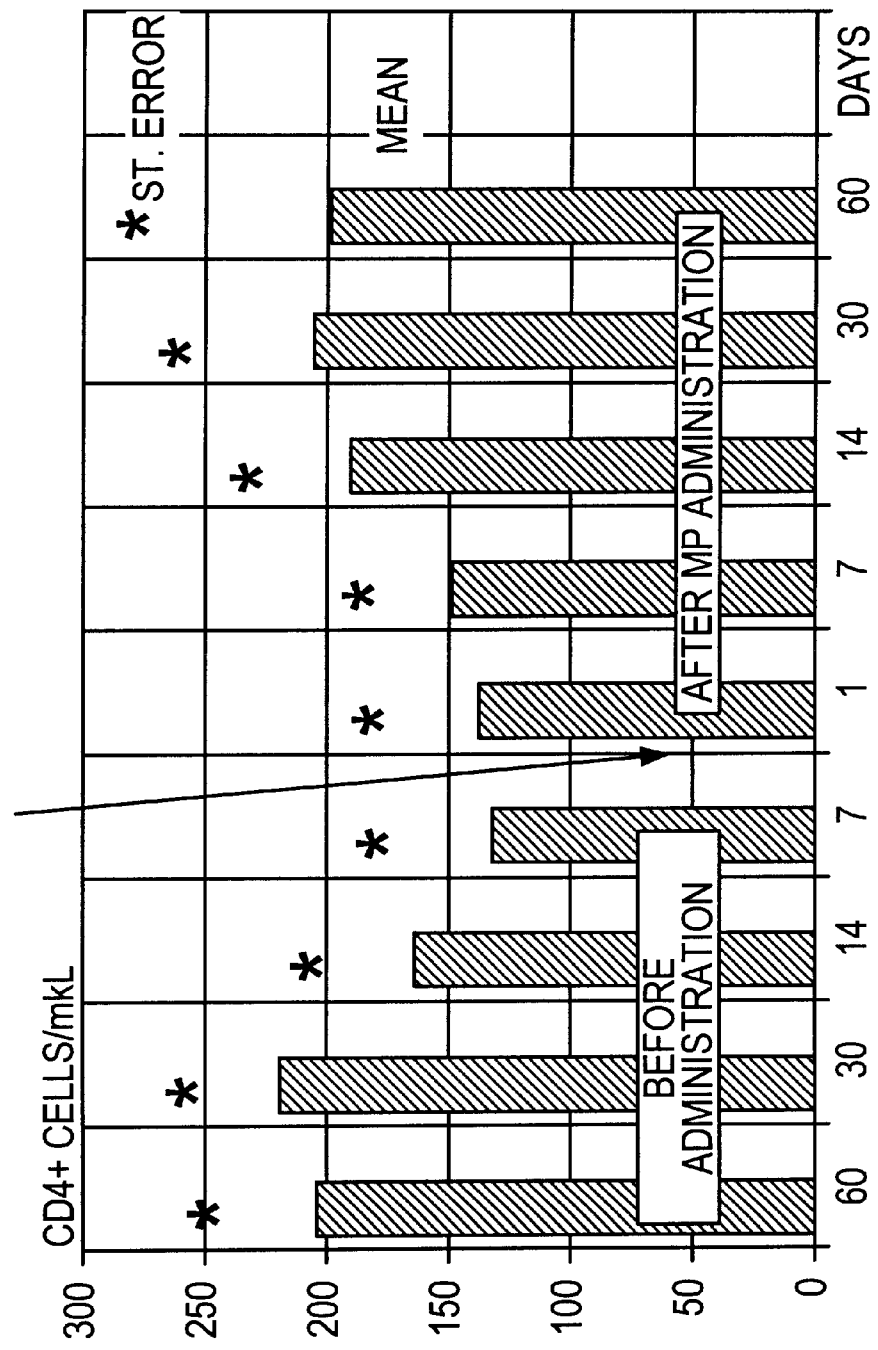
FIG. 18 is a graph of dynamic of CD4+ lymphocytes in 15 patients with sharp decrease of CD4+ (more than 100 CD4+ Cell/L within 6 months) prior administration of medicinal preparation.

The data on variations of levels of CD4, CD3 and CD8 depicted in FIG. 17 evidence that administration of the medicinal preparation results in two-phase, i.e. after 2 weeks and 2 months, increase in the level of these indices, being statistically valid for CD4 and CD3.

In the control group, no substantial changes of immunologic indices that would have a certain trend were noted (Table 1.3)

TABLE 3

Dynamic of immunology indices in the control group of AIDS patients (treated by conventional methods at the same specialized for AIDS clinic) during 2 months

| Index |  | Period of observation (N = 25) |  |  |  |
|---|---|---|---|---|---|
|  |  | 1st day | 14th day | 30th day | 60th day |
| CD4+ | M | 385.9 | 378.6 | 451.6 | 524.9 |
|  | m | 47.2 | 48.3 | 81.0 | 91.9 |
|  | p |  | >0.05 | >0.05 | >0.05 |
| CD8+ | M | 971.4 | 951.2 | 920.9 | 821.6 |
|  | m | 140.0 | 158.6 | 173.9 | 131.3 |
|  | p |  | >0.05 | >0.05 | >0.05 |
| CD4+/CD8+ | M | 0.71 | 0.66 | 0.86 | 0.73 |
|  | m | 0.12 | 0.09 | 0.16 | 0.10 |
|  | p |  | >0.05 | 0.35 | >0.05 |
| CD3+ | M | 1208.7 | 1135.7 | 1370.7 | 1252.4 |
|  | m | 173.2 | 163.1 | 202.0 | 191.6 |
|  | p |  | >0.05 | >0.05 | >0.05 |
| Leukocytes | M | 2560.4 | 2468.9 | 2894.3 | 2724.5 |
|  | m | 193.3 | 177.1 | 239.6 | 1097.8 |
|  | p |  | >0.05 | >0.05 | >0.05 |

Given below are changes of immunoligic status in patients suffering from ARC (Table 4).

TABLE 4

Dynamic of CD4+ in patients with AIDS related complex (AIDS ARC) after administration of Medicinal preparation

| Statistic indices | units | N | T | p | Min | Max | Mean | St. err. |
|---|---|---|---|---|---|---|---|---|
| Before | abs | 26 |  |  | 15 | 631 | 232.8 | 35.5 |
| treatment | % | 26 |  |  | 1.1 | 34.6 | 12.1 | 1.8 |
| After | abs | 26 | 0.0 | >0.05 | 17 | 821 | 232.1 | 39.4 |
| 7 days | % | 26 | 0.3 | >0.05 | 1.2 | 38.0 | 12.3 | 1.9 |
| After | abs | 26 | 2.1 | 0.042 | 20 | 1115 | 324.9 | 60.4 |
| 14 days | % | 26 | 1.9 | >0.05 | 1.3 | 35.0 | 13.9 | 1.9 |
| After | abs | 26 | 1.3 | >0.05 | 10 | 956 | 281.9 | 47.7 |
| 30 days | % | 26 | 0.5 | >0.05 | 1.2 | 33.0 | 12.6 | 1.7 |
| After | abs | 13 | 2.3 | 0.037 | 15 | 839 | 351.5 | 78.2 |
| 60 days | % | 13 | 1.0 | >0.05 | 1.1 | 23.0 | 14.9 | 2.6 |

Given below are data on changes of immunologic status in patients having clinical symptoms of AIDS (table 5).

TABLE 5

Dynamic of CD4+ in AIDS patients afret administration of Medicinal preparation

| Statistic indices | units | N | T | p | Min | Max | Mean | St. err. |
|---|---|---|---|---|---|---|---|---|
| Before | abs | 8 |  |  | 6 | 189 | 43.1 | 21.3 |
| treatment | % | 8 |  |  | 1.1 | 20.0 | 5.5 | 2.2 |
| After | abs | 8 | 2.8 | 0.026 | 0 | 288 | 80.1 | 32.4 |

TABLE 5-continued

Dynamic of CD4+ in AIDS patients afret administration of Medicinal preparation

| Statistic indices | units | N | T | p | Min | Max | Mean | St. err. |
|---|---|---|---|---|---|---|---|---|
| 7 days | % | 8 | 1.4 | >0.05 | 0 | 19.6 | 7.4 | 2.5 |
| After | abs | 8 | 2.5 | 0.043 | 3 | 272 | 86.6 | 32.7 |
| 14 days | % | 8 | 0.6 | >0.05 | 0.7 | 16.6 | 6.5 | 1.9 |
| After | abs | 8 | 0.7 | >0.05 | 3 | 174 | 64.6 | 20.3 |
| 30 days | % | 8 | 0.4 | >0.05 | 0.7 | 16.6 | 6.4 | 1.8 |
| After | abs | 3 | 1.3 | >0.05 | 22 | 47 | 36.3 | 7.4 |
| 60 days | % | 3 | 1.3 | >0.05 | 1.6 | 16.6 | 7.4 | 4.7 |

Medicinal preparation provides substantial support to patients suffering from HIV-disease, and in which the condition assessment corresponds to Karnofsky Index of 70–80 points and lower, as well as to patients in which the value of Karnofsky Index decreased by 20 points during last 6 months. Dynamics of the amount of helpers in patients versus Karnofsky Index is shown in Table 1.6.

Medicinal preparation combined with c antiretroviral therapy

Some patients received antiretroviral therapy during several months, however without any results. Separated are 10 patients that received azidotimidin during 2, 3 or 4 months prior to administration of Medicinal preparation, and continued receiving such therapy after administration. No substantial reactions of intolerance were noted. Obviously, as a result of development of resistance against AZT, these patients demonstrated negative dynamics of the amount of CD4+ lymphocytes against the background of azidotimidin administration; at the same time, a statistically valid decrease by 150 cells or 58% (p=o.025) was observed as against the moment of administration of Medicinal preparation. These patients did not receive any antiretroviral therapy. Immunologic monitoring in patients that received antiretroviral therapy prior to and after administration of Medicinal preparation is shown in Table 1.8 (5.3) and FIG. 19.

TABLE 6

Dynamic of CD4+ in AIDS patients with different level karnofsky's index after administration of Medicinal preparation

| Karnofsky's Index | Stat. index | Period of observation after administration of medicinal preparation | | | | |
|---|---|---|---|---|---|---|
| | | Before | 7 days after | 14 days after | 30 days after | 60 days after |
| 90–100 | M | 220.4 | 236.8 | 295.3 | 244.5 | 300.6 |
| | m | 44.2 | 53.2 | 74.8 | 60.9 | 90.5 |
| | p | | >0.05 | <0.05 | >0.05 | <0.05 |
| | N | 17 | 17 | 17 | 17 | 11 |
| 70–80 | M | 221.8 | 220.7 | 303.8 | 265.3 | 255.4 |
| | m | 84.0 | 81.1 | 175.4 | 124.4 | 103.1 |
| | p | | >0.05 | <0.05 | <0.05 | >0.05 |
| | N | 6 | 6 | 6 | 6 | 5 |
| 40–50 | M | 150.7 | 120.1 | 174.1 | 208.1 | 158.5 |
| | m | 70.4 | 49.8 | 59.7 | 58.3 | 136.5 |
| | p | | >0.05 | <0.05 | <0.05 | >0.05 |
| | N | 7 | 7 | 7 | 7 | 7 |
| 10–20 | M | 66.5 | 119.0 | 133.8 | 68.0 | |
| | m | 41.2 | 59.2 | 55.9 | 20.4 | |
| | p | >0.05 | >0.05 | >0.05 | >0.05 | |
| | N | 4 | 4 | 4 | 4 | 0 |

TABLE 7

Dynamic of CD4+ and CD8+ lymphocytes in patients with sharp decrease of CD4+ (more that 100 CD4+ cells/µL within 6 months) prior administration of Medicinal preparation (N = 15)

| | Period of observation before administration of Medicinal preparation (days) | | | | Day after Med. Prep. administration | Period of observation after administration of Medicinal preparation (days) | | | |
|---|---|---|---|---|---|---|---|---|---|
| | 60 | 30 | 14 | 7 | 1 | 7 | 14 | 30 | 60 |
| CD4+ M | 205.7 | 219.8 | 164.1 | 130.9 | 136.8 | 147.4 | 188.7 | 206.2 | 197.5 |
| m | 44.6 | 40.7 | 48.0 | 44.6 | 40.4 | 34.0 | 35.7 | 56.7 | 82.2 |
| p | | >0.05 | >0.05 | <0.05 | | >0.05 | >0.05 | <0.05 | <0.05 |
| CD8+ M | 829.7 | 977.5 | 1178 | 934.0 | 996.2 | 11560 | 1110 | 1088 | 873.0 |
| m | 221.9 | 279.9 | 314.8 | 258.6 | 237.3 | 313.6 | 301.7 | 323.1 | 350.3 |
| p | | >0.05 | >0.05 | >0.05 | | >0.05 | >0.05 | >0.05 | >0.05 |

TABLE 8

Dynamic of CD4+ lymphocytes in AIDS patients, that received antiretroviral therapy, after administration of Medicinal preparation (N = 10)

| | Period of observation before administration of Medicinal preparation (days) | | | | Day after Med. Prep. administration | Period of observation after administration of Medicinal preparation (days) | | | |
|---|---|---|---|---|---|---|---|---|---|
| CD4+ | 60 | 30 | 14 | 7 | 1 | 7 | 14 | 30 | 60 |
| M | 260.7 | 223.5 | 160.5 | 96.5 | 110.4 | 146.9 | 180.7 | 199.9 | 197.5 |
| m | 60.9 | 45.1 | 55.3 | 25.7 | 33.6 | 37.5 | 38.4 | 62.2 | 82.2 |
| Min | 41 | 44 | 30 | 8 | 9 | 41 | 41 | 47 | 22 |
| Max | 614 | 431 | 440 | 189 | 376 | 429 | 389 | 700 | 533 |
| p | | >0.05 | >0.05 | <0.05 | | 0.025 | 0.017 | 0.068 | 0.054 |

Viral load 14 days after transplantation, observed in 10 patients (table 9) was an increase in the viral load; in 3 patients this load decreased, and in I patient it remained almost the same; amount of CD4+ cells increased in 4 patients, decreased in 6 patients, and remained unchanged in 2 patients. 30 days later, viral load increased in 4 patients, decreased in 5, and remained the same in I patient, while amount of CD4+ cells increased 4 patients, decreased in 5, and remained the same in 2 patients. With regard to joint dynamics, concurrent increase in the viral load and CD4+ amount was observed in 4 cases, and concurrent decrease in 3 cases; load increase and decrease in CD4+ lymphocytes was observed in 7 cases; load decrease and CD4+ increase, in 5 cases; load increase with stable CD4+, in 3 cases; load decrease with stable CD4+, in 1 case; with stable viral load, CD4+increased in I case and decreased in I case.

TABLE 9

Corresponding levels of CD4+ and Viral load in AIDS patients after administration of Medicinal preparation

| | Before administration of Medicinal preparation | | 14 days after administration of Medicinal preparation | | 30 days after administration of Medicinal preparation | |
|---|---|---|---|---|---|---|
| Case | Viral load | CD4+ | Viral load | CD4+ | Viral load | CD4+ |
| 1 | 3900 | 392 | 4000 | 945 | no data | |
| 2 | 5300 | 460 | 3300 | 491 | no data | |
| 3 | 10200 | 205 | 74000 | 161 | 187000 | 167 |
| 4 | 12587 | 301 | 29210 | 308 | 3318 | 462 |
| 5 | 14300 | 90 | 69500 | 70 | 14000 | 80 |
| 6 | 15700 | 19 | 14000 | 20 | 122000 | 10 |
| 7 | 24300 | 160 | 13400 | 260 | 28800 | 120 |
| 8 | 26800 | 382 | 45200 | 277 | 20600 | 364 |
| 9 | 27300 | 73 | 29208 | 116 | 29208 | 82 |
| 10 | 37025 | 20 | 88400 | 31 | 43200 | 15 |
| 11 | 47000 | 15 | 50600 | 31 | 43400 | 15 |
| 12 | 87700 | 160 | 30000 | 106 | 41600 | 180 |
| 13 | 99669 | 6 | 679439 | 0 | died | |
| 14 | 136000 | 51 | 223000 | 25 | 107000 | 25 |

Syndromes of early improvement and changes in the psychophysical state of patient upon administration of Medicinal preparation Most frequently, observed in patients was general weakness, fast fatiguability, loss of weight, temperature increase, headache and pain in joints. Upon administration of the fetal liver suspension, usually during two weeks, improvement was observed in patients, which was best manifested in patients suffering from astheno-neurotic syndrome (Table 10).

TABLE 10

Symptoms of mitigation of astheno-neurotic syndrome in AIDS patients after administration of Medicinal preparation

| | Whole group (N = 38) | | Patients with astheno-neurotic syndrome | |
|---|---|---|---|---|
| Feature | abs | % | abs | % |
| Increasing of energy level | 17 | 45 | 14 | 64 |
| Improving of appetites | 13 | 34 | 11 | 50 |
| Normalization of sleeping | 15 | 39 | 13 | 59 |
| Pain decrease | 5 | 13 | 4 | 18 |
| Diminishing of irritation | 12 | 32 | 12 | 55 |
| Increasing of work capability | 7 | 18 | 6 | 27 |
| Decreasing of fatigue | 14 | 37 | 11 | 50 |
| Improvement of mood | 21 | 55 | 17 | 77 |

Detailed description of the use of the present invention in compliance with the clinical practice available with the author is given in the following Examples.

EXAMPLE 1

Female patient 920034 "T", 37 years old, was admitted to the AIDS Department of the Kiev Research Institute for Epidemiology and Infectious Diseases on Feb. 23, 1993.

Diagnosis: clinical AIDS; pneumocystic pneumonia in the reconvalescence stage; chronic smoker's bronchitis; post-encephalitis state; candidiasis of intestine and respiratory tracts; chronic gastritis at the unstable remission stage; chronic cholecystitis at the unstable remission stage.

HIV infection was revealed in 1990; the patient was treated in Moscow till September, 1992. Her first stay with the AIDS Department of the Kiev Research Institute for Epidemiology and Infectious Diseases lasted from Sep. 17 till Oct. 26, 1992. The patient suffered from pneumocystic pneumonia.

On Oct. 23, 1992, the patient was transferred to resuscitation department with herpetic encephalitis; here, after the spinal puncture, spastic paraplegia and fallopian neuritis developed as a result of encephalitis.

The patient complained permanent headaches that were periodically aggravated, accompanied by nausea and sometimes by vomiting, as well as vertigo and periodic losses of consciousness. In addition, the patient suffered from cough accompanied by expectoration of small amounts of sputum, sensation of pain in bones and joints, weakness of muscles in lower extremities (walking while holding a support), facial asymmetry (right-side neuritis of the facial nerve). Body temperature periodically increased up to 39° C.

Objectively: intugements were pale and clean; small peripheric lymph nodes (up to 0.5 cm in diameter), movable, of elastic consistence, painless. Cardiac sounds were clear and rhythmic; respiration in lungs was rough, with diffused dry rale over the total surface.

The abdomen was soft and sensitive to palpation in the epigastric and right hypochondrium areas; stools and diuresis without any peculiarities.

Medicinal preparation was administered on Mar. 4, 1993 in an amount of 2.5 ml (characteristics: the contents of nucleated cells is 98'10$^6$/ml, CFU GM 26 10$^3$/ml, CFU GEMM 1.4 10$^3$/ml, the contents of progenitor cells (CD34) is 2.4'10$^6$/ml). Way of administration: intravenous (Tables 11, 12).

After administration of Medicinal preparation, positive dynamics was observed, i.e. improvement of general state, emotional tonus and appetite. After several days, the cough decreased; it became easier for the patient to walk, improvement of coordination and headache decrease were observed, fever diminished. Rough respiration was still present in the lungs, however no rale was auscultated.

On Apr. 29, 1993, repeated administration of Medicinal preparation was carried out (the same sample, in amount of 2.5 ml). The patient was discharged on Apr. 30, 1993 (for family reasons) in the satisfactory state.

The patient stayed once again at the AIDS Department from May 13 till Jul. 17, 1993. Headache, vertigo, pain in bones and joints were still present. Body temperature however did not increase; good appetite and sleep were observed; facial asymmetry diminished, cough disappeared; the patient could walk small distances without any support.

TABLE 11

Dynamics of peripheral blood indices in female patient T.
(The patient from example 1. Observation is being continued)

| Date | Erythrocytes 10$^{12}$/l | Hemoglobin, g/l | Color index | Leukocytes, 10$^9$/l | Baso phils, % | Eosino- phils, % | Related to slab neutrphile, % | Segment nuclear, % | Lymphocytes, % | Monocytes, % | S.R., mm/hr |
|---|---|---|---|---|---|---|---|---|---|---|---|
| 25.02.93 | 4.0 | 129 | 0.9 | 8.8 | 1 | | 1 | 68 | 25 | 5 | 53 |
| 04.03.93 | 1 transplantation | | | | | | | | | | |
| 09.03.93 | 4.0 | 119 | 0.9 | 7.7 | | 3 | 1 | 40 | 42 | 5 | 60 |
| 18.03.93 | 4.0 | 119 | 0.9 | 8.9 | | | | | | | |
| 01.04.93 | 4.0 | 120 | 0.9 | 7.8 | 1 | 2 | 1 | 47 | 46 | 4 | 45 |
| 13.04.93 | 4.0 | 128 | 0.9 | 7.6 | 1 | 3 | 1 | 40 | 50 | 6 | 33 |
| 29.04.93 | 2 transplantation | | | | | | | | | | |
| 18.05.93 | 4.0 | 132 | 0.9 | 8.9 | | 2 | 2 | 40 | 46 | 2 | 45 |
| 01.06.93 | 2.9 | 100 | | 6.4 | 1 | 1 | 1 | 50 | 43 | 4 | 38 |
| 08.07.93 | 3.8 | 115 | | 4.0 | 1 | 2 | 3 | 66 | 25 | 3 | 40 |
| 01.08.93 | | | | 6.2 | 1 | 3 | 4 | 67 | 23 | 2 | 21 |
| 21.09.93 | 4.1 | 130 | 0.9 | 3.5 | | 2 | 1 | 44 | 50 | 3 | 59 |
| 07.10.93 | | | | 4.4 | 1 | | 1 | 64 | 26 | 5 | 58 |
| 02.11.93 | 4.1 | 129 | 0.9 | 3.8 | 1 | 2 | 2 | 60 | 30 | 5 | 44 |
| 05.011.93 | 3 transplantation | | | | | | | | | | |
| 11.11.93 | 4.0 | 130 | 0.9 | 3.9 | 2 | 2 | 1 | 60 | 31 | 4 | 60 |
| 23.11.93 | 4.1 | 129 | 0.9 | 3.4 | 0 | 2 | 1 | 65 | 26 | 3 | 48 |
| 07.12.93 | 4.1 | 129 | 0.9 | 3.9 | 0 | 2 | 2 | 60 | 33 | 3 | 57 |
| 06.01.94 | 4.1 | 130 | 0.9 | 3.7 | 0 | 2 | 1 | 47 | 47 | 3 | 42 |
| 10.02.94 | 4.0 | 129 | 0.9 | 3.6 | 1 | 2 | 2 | 40 | 49 | 6 | 38 |
| 17.03.94 | 4.2 | 129 | 0.9 | 3.8 | 1 | 1 | 1 | 37 | 57 | 3 | 21 |
| 04.10.94 | 4.0 | 121 | 0.9 | 3.1 | 0 | 2 | 2 | 56 | 36 | 4 | 33 |
| 19.01.95 | 3.2 | 98 | 0.9 | 2.6 | 1 | 1 | 3 | 45 | 44 | 6 | 28 |
| 15.03.95 | 3.8 | 118 | 0.9 | 4.2 | 1 | 2 | 2 | 67 | 22 | 6 | 28 |
| 16.03.95 | 4 transplantation | | | | | | | | | | |
| 20.04.95 | 4.2 | 126 | 0.9 | 5.0 | 1 | 3 | 2 | 52 | 34 | 8 | 25 |
| 15.09.95 | 4.0 | 111 | 0.9 | 3.7 | 0 | 4 | 1 | 60 | 33 | 2 | 31 |
| 13.04.96 | 3.6 | 102 | 0.9 | 3.5 | 1 | 3 | 2 | 67 | 26 | 1 | 30 |
| 16.04.96 | 5 transplantation | | | | | | | | | | |
| 17.05.96 | 3.8 | 122 | 1.0 | 4.2 | 0 | 3 | 3 | 54 | 36 | 4 | 28 |
| 14.10.96 | 3.3 | 105 | 0.9 | 3.8 | 1 | 2 | 2 | 54 | 35 | 6 | 28 |
| 2.08.97 | 3.2 | 102 | 0.8 | 3.2 | 0 | 1 | 6 | 62 | 23 | 8 | 44 |
| 06.08.97 | 6 transplantation | | | | | | | | | | |
| 8.12.97 | 3.6 | 124 | 0.9 | 4.8 | 1 | 2 | 4 | 59 | 24 | 10 | 26 |

TABLE 12

Dynamics of immune indices in female patient T.
(The patient from example 1. Observation is being continued)

| Date dd.mm.yy | CD3+ abs num. in mm3 % | CD4+ abs num. in mm3 % | CD8+ abs num. in mm3 % | HLADR abs num. in mm3 % | CD4/ CD8 | SIg abs num. in mm3 % |
|---|---|---|---|---|---|---|
| 25.02.93 | 950 | 442 | 851 | 85 | 0.52 | 466 |
|  | 43.2 | 20.1 | 38.7 | 3.9 |  | 21.2 |
| 04.03.93 | 1 transplantation | | | | | |
| 09.03.93 | 407 | 414 | 405 | 453 | 1.02 | 252 |
|  | 23.2 | 23.7 | 23.2 | 25.9 |  | 14.4 |
| 18.03.93 | 1807 | 1115 | 572 | 594 | 1.94 | 449 |
|  | 42.3 | 26.1 | 13.4 | 19.9 |  | 10.5 |
| 01.04.93 | 1690 | 793 | 377 | 384 | 2.1 | 459 |
|  | 47.1 | 22.1 | 10.5 | 10.7 |  | 12.8 |
| 13.04.93 | 1512 | 604 | 840 | 380 | 0.72 | 433 |
|  | 39.8 | 15.9 | 22.9 | 10.2 |  | 11.4 |
| 29.04.93 | 2 transplantation | | | | | |
| 18.05.93 | 1641 | 528 | 810 | 394 | 0.65 | 438 |
|  | 40.1 | 12.9 | 19.8 | 8.9 |  | 10.7 |
| 01.06.93 | 1016 | 439 | 632 | 468 | 0.69 | 335 |
|  | 36.1 | 15.6 | 26.4 | 16.6 |  | 11.9 |
| 08.06.93 | 349 | 211 | 130 | 120 | 1.63 | 60 |
|  | 34.4 | 21.2 | 13.0 | 12.0 |  | 6.0 |
| 01.07.93 | 497 | 369 | 310 | 219 | 1.19 | 233 |
|  | 34.9 | 25.9 | 21.8 | 15.4 |  | 16.4 |
| 21.09.93 | 838 | 393 | 213 | 497 | 1.85 | 385 |
|  | 47.9 | 22.5 | 12.2 | 28.4 |  | 22.0 |
| 07.10.93 | 464 | 243 | 297 | 65 | 0.82 | 275 |
|  | 40.6 | 21.3 | 26.0 | 5.7 |  | 24.1 |
| 02.11.93 | 479 | 247 | 223 | 184 | 1.1 | 197 |
|  | 31.5 | 16.3 | 14.7 | 12.1 |  | 13.0 |
| 05.11.93 | 3 transplantation | | | | | |
| 11.11.93 | 512 | 340 | 275 | 165 | 1.23 | 82 |
|  | 33.7 | 22.4 | 18.1 | 10.9 |  | 5.4 |
| 23.11.93 | 319 | 87 | 83 | 183 | 1.04 | 91 |
|  | 31.6 | 9.9 | 9.5 | 20.8 |  | 10.4 |
| 07.12.93 | 284 | 160 | 204 | 90 | 0.78 | 137 |
|  | 22.1 | 12.5 | 15.9 | 7 |  | 10.7 |
| 06.01.94 | 763 | 347 | 507 | 330 | 0.68 | 358 |
|  | 43.9 | 20 | 29.2 | 19 |  | 20.5 |
| 10.02.94 | 1184 | 159 | 487 | 398 | 0.33 | 311 |
|  | 70 | 9.4 | 28.8 | 23.5 |  | 18.4 |
| 17.03.94 | 1113 | 400 | 1072 | 258 | 0.37 | 147 |
|  | 51.4 | 18.5 | 49.5 | 11.9 |  | 6.8 |
| 04.10.94 | 737 | 308 | 544 | 176 | 0.51 | 34 |
|  | 67.0 | 28.0 | 55.0 | 16.0 |  | 3.1 |
| 15.03.95 | 499 | 143 | 323 | 213 | 0.44 | 240 |
|  | 54.0 | 15.5 | 35.0 | 23.0 |  | 26.0 |
| 16.03.95 | 4 transplantation | | | | | |
| 20.04.95 | 1003 | 357 | 510 | 255 | 0.70 | 408 |
|  | 59.0 | 21.0 | 30.0 | 15.0 |  | 24.0 |
| 15.09.95 | 928 | 379 | 501 | 220 | 0.76 | 354 |
|  | 76.0 | 31.0 | 41.0 | 18.0 |  | 29.0 |
| 13.04.96 | 619 | 291 | 528 | 155 | 0.55 | 200 |
|  | 68.0 | 32 | 58 | 17 |  | 22 |
| 16.04.96 | 5 transplantation | | | | | |
| 17.05.96 | 862 | 423 | 650 | 302 | 0.65 | 348 |
|  | 57 | 28 | 43 | 20 |  | 23 |
| 14.10.96 | 718 | 359 | 625 | 359 | 0.57 | 253 |
|  | 54 | 27 | 47 | 27 |  | 19 |
| 02.08.97 | 294 | 84 | 192 | 115 | 0.43 | no data |
|  | 40 | 11.4 | 26 | 15.6 |  |  |
| 06.08.97 | 6 transplantation | | | | | |
| 08.12.97 | 599 | 204 | 340 | 253 | 0.6 | no data |
|  | 52 | 17.7 | 29 | 22 |  |  |

After her discharge on Jul. 17, 1993, the patient stayed at home in the city of Odessa where she endured herpes zoster of the hairy part of the head, accompanied by the body temperature increase and encephalopathy. Breakouts continued till Aug. 4, 1993.

On Sep. 9, 1993, the patient was admitted to the AIDS Department with complaints of referred headache to right and left orbital cavities, aching pain and hindered movements in joints, increasing body temperature up to 37.3 to 38.2° C., aching epigastric pain, and cough accompanied by expectoration of thick of sputum having a purulent nature. Rough respiration was auscultated in the lungs together with dry rale on both sides (Oct. 19, 1993: pneumocysts in 48% of visual fields).

On Nov. 5 1993, third administration of the same sample of Medicinal preparation (1.5 ml) when observed decrease in the amount of CD4 lymphocytes was down to 160 cells/$\mu$l. Increase in the CD4 amount was up to 340 cells, and was maintained constant during two months. The patient noted an improvement of general state, decrease of cough, headache, improvement of sleep and spirits. 3 months later, amount of CD4 cells decreased down to 160/$\mu$l, clinical state however remained stable. The patient did not apply for medical assistance during almost 18 months, till March 1995, when symptoms of bronchitis again became more pronounced, weakness started progressing, depression appeared, walk and coordination of movements deteriorated.

On Mar. 16, 1995, the fourth treatment session was carried out with the use of Medicinal preparation in an amount of 2 ml (new sample).

One year later, on Apr. 16, 1996, 2 ml of the same sample of Medicinal preparation were administered.

Upon administration of Medicinal preparation, the patient always noted availability of the early improvement syndrome, stabilization of psychoemotional status, improvement of walk mental and physical ability. Manifestations of chronic brinchitis and pyelonephritis substantially decreased.

In August, 1997, the patient endured serious and acute right-hand pneumonia; she was treated at the Odessa Oblast Center for AIDS Prevention and Control On Aug. 6, 1998, the patient received the remaining portion of her second dose of Medicinal preparation in an amount of 1.5 ml. In addition, massive antibiotics therapy was carried out. After two weeks, general condition of the patient improved: weakness and sweating disappeared, cough decreased, motion and appetite improved. The patient was discharged 6 weeks after administration of Medicinal preparation in a satisfactory condition and 2.5 kg weight gain.

In 1998, she contacted physicians of the Cell Therapy Clinic on the telephone. The patient noted that her condition was stable, although occasional depression episodes, increase of weakness, sweating and temperature increases occurred.

At present, condition of the patient is satisfactory, and observation keeps on going.

EXAMPLE 2

Male patient Sh., 47 years old, stayed at the AIDS Department of the Kiev Research Institute for Epidemiology and Infectious Diseases in February and March, 1993.

HIV infection was diagnosed in 1993 (the way of infection was not identified: the detection of infection was preceded by frequent hospitalizations and numerous injections caused by iron deficiency anemia. P. carinii were found in his sputum; however no clinical symptoms of pneumocystic pneumonia were observed despite the fact that the patient could not endure Biceptol prophylactics because of intolerance. In the course of several years, the patient suffered from hemorrhoids with frequent hemorrhages, iron deficiency anemia and chronic hepatitis. The patient however maintained ability to work as a long-distance truck driver. The value of Karnofsky Index was 80 points. The patient was losing ability to work as a long-distance truck driver.

Diagnosis: HIV infection; persisting generalized lymphadenopathy; chronic bronchitis at the unstable remission stage; iron deficiency anemia; II stage hemorrhoids; chronic persisting hepatitis at the unstable remission stage.

On Mar. 4, 1993, the day when he received Medicinal preparation, the patient complained increased fatiguability, vertigo, headache, weakness, and moderate dry cough.

Objective examination revealed increased lymph nodes (>1 cm) in inguinal, axillary and posterocervical areas.

Scattered dry rale was auscultated in lungs. Liver edge was protruding from beyond the costal arch by 4 cm. At the beginning of observation, the level of hemoglobin in blood tests was 68 g/l; erythrocytes, 3.5 g/l. Absolute amount of CD4+ lymphocytes was 631/mm$^3$.

Medicinal preparation was administered intravenously, in drops. No side reactions were noted during administration and in the course of 2-hour observation. Upon administration of Medicinal preparation, the patient did not note any substantial changes; however appetite and general state slightly improved. During subsequent 60 days, monitoring of laboratory indices was carried out. Red blood tests revealed certain improvement of hemoglobin indices (up to 79 g/l by the end of observation); amount of erythrocytes however did not change considerably. On the contrary, immunologic monitoring revealed substantial changes: after 14 days, amount of CD4+ lymphocytes increased up to 1107/mm$^3$, and by the end of observation it was 839/mm$^3$ (although 30 days later sudden decrease down to 382/mm$^3$ was noted).

The patient was discharged from the hospital in a satisfactory condition and went back to labor activities. Kamofsky Index increased up to 100 points. The patient did not turn to clinic any more. In December, 1993, he died in a district hospital from disseminated form of tuberculosis.

EXAMPLE 3

Female patient F., 23 years old, was infected by heterosexual way. The patient was in the condition of irritative weakness: combination of elevated erethism and excitability, and increased fatiguability and emaciation. Emotional reactions featured excessive strength and fast emaciation. Irritation reactions were caused by insignificant reasons; in addition, there was a feeling of dissatisfaction with surrounding people, and decreased ability to control external manifestations of her emotions. Spirits were unstable, and a trend to concentrate on her own painful feelings was noted. The patient suffered from frequent catarrhal diseases (several times a year), prolonged cough accompanied by expectoration of small amounts of sputum (total duration of more than 2 months a year), headache, bad sleep, periodic palpitation in the middle of the night, weakness, and quick fatigue. In addition, herpetic eruption on the body occurred 2 to 3 times a year which regressed only upon treatment with acyclovir. Dissipated dry rale was auscultated in the lungs. Diagnosis: HIV infection; chronic recurring simple herpes; chronic bronchitis in the unstable remission stage; neurocirculatory mixed-type dystonia. Karnofsky Index was 100. In addition, the patient's social adaptation was poor; she stayed at the hostel in permanent fear of diagnosis disclosure; her husband (who infected her) was in prison; she did not expect any support from other members of her family.

On April 20, Medicinal preparation was administered intravenously (1.5 ml were administered, amount of cells being $12*10^6$/ml, CFU GM—$25*10^3$/ml, CFU GEMM—3, $7*103$/ml, $CD_{34}$–$2,8*10^6$/ml.). The patient endured administration of Medicinal preparation satisfactorily, and in the second half of the same day noted substantial improvement of appetite. Possibly, due to the change of diet late at night (according to patient's words, she had too much fried potato), she had the feeling of inner trembling and bad sleep. During next few days however she felt substantial improvement of spirits, her sleep became more quiet (before, she had to take sedative preparations); feeling of fear and concern about the future decreased, physical activity improved; the patient became more energetic, helped her roommates, cooperated with the hospital personnel (this fact was confirmed by nurses). Communication with other people became more friendly.

In the day of administration of Medicinal preparation, amount of CD4+ lymphocytes was 100 cells/mm$^3$; 7 days later, 207/ mm$^3$; 14 days later, 396/ mm$^3$; an increased level was maintained during 60 days (268/ mm3;). Other immune system cells (absolute amount of lymphocytes, CD3+, CD8+) generally followed the same dynamics. The cough became weaker, amount of dry rale in lungs decreased. The patient was discharged from the hospital in satisfactory condition.

The need of repeated hospitalization appeared three months later when aggravation of chronic bronchitis occurred after supercooling; besides, there was a relapse of simple herpes. Amount of CD4+ lymphocytes decreased down to 100 cells/ mm$^3$. Antimicrobe therapy was carried out with the use of Biceptol, and antiretoviral therapy with the use of acyclovir.

On Apr. 4, 1995, repeated administration of Medicinal preparation was carried out (the same sample, 1.4 ml, intravenously in drops). The patient endured administration satisfactorily. Upon administration of Medicinal preparation, during 5 days the patient stated substantial improvement of appetite and spirits, decrease of headache, increase of energy, and a wish to increase physical activities. During the next week, the patient stated decrease of cough and sweating, normalization of temperature. Herpetic injuries regressed, amount of rale in lungs decreased. The patient was discharged in the satisfactory condition. 6 months after repeated administration of Medicinal preparation, amount of CD4+ lymphocytes in this patient was 253 cells/ mm$^3$.

On Feb. 13, 1996, the patient came for examination due to pregnancy; at that time, amount of CD4+ lymphocytes was 142 cells/ mm$^3$. She was warned about the risk of pregnancy (possibility of quick progress of HIV infection to AIDS), as well as probability of child's infection. The patient however was confident about herself and her right to make a decision on delivery; she was sure about her ability to handle any problems. After delivery, the patient has been under observation at the location of her residence.

EXAMPLE 4

Male patient 900007 "G" was admitted to the AIDS Department of the Kiev Research Institute for Epidemiology and Infectious Diseases on May 31, 1993.

Diagnosis: HIV infection, carrier; chronic smoker's bronchitis.

HIV infection was revealed in 1990, during patient's stay at a hospital for the reason of acute cholecystitis. From May 17 till Jun. 7, 1993, the patient was treated at the AIDS department on occasion of the lacunar angina; since that time he has been on dispensary register and observed periodically.

On Jun. 3, 1993, the patient was subjected to administration of Medicinal preparation in an amount of 3 ml, amount of nucleated cells being $78*10^6$/ml, CFU GM—$44'*10^3$/ml, CFU GEMM—$2,4*10^3$/ml, CD34—$2,7*10^6$/ml). Method of administration was intravenous. The patient endured administration of Medicinal preparation satisfactorily; no changes in his state were noted.

Since Jul. 23, 1993, the patient was treated at the AIDS Department on occasion of acute left lower-lobe pneumonia. (Roentgenography of thorax organs, taken on Jul. 23, 1993: infiltrative changes in the form of focal shades in the lower lobe of the left lung; the root is reactive; the right lung without any peculiarities). No pneumocystes were revealed in the course of sputum tests. General state demonstrated expressed weakness, sweating, and cough with expectoration of small amounts of sputum. For 20 days the patient received doxycyclin, biceptol, and nistatin; upon completion of the treatment course, he was discharged in the satisfactory state.

On Sep. 1, 1993, the repeated administration of Medicinal preparation of cryopreserved cell suspension (the same sample) was carried out, the patient endured this administration of Medicinal preparation satisfactorily. On Sep. 16, 1993, an increase in the body temperature of up to 37.7° C. was noted; it was accompanied by weakness, pains and aches throughout the body, and headache. On Sep. 17, 1993, the state normalized.

Tables 13 through 18 give the results of laboratory and immunologic tests. On Sep. 24, 1993, the patient was discharged in the satisfactory state. Patient up to now is asymptomatic HIV-positive with CD4 level over 500 cells/ mkl.

TABLE 13

Dynamics of peripheral blood indices in male patient G.

| Date | Erythrocytes, $10^{12}$/l | Hemoglobin, g/l | Color index | Leukocytes, $10^9$/l | Basophils, % | Eosinophils, % | Related to slab neutrophils, % | Segmentnuclear, % | Lymphocytes, % | Monocytes, % | S. R., mm/hr |
|---|---|---|---|---|---|---|---|---|---|---|---|
| 01.06.93 | 4.7 | 155 | 0.9 | 3.9 | 1 | 1 | 1 | 59 | 37 | 2 | 7 |
| 08.06.93 | 4.8 | 155 | | 4.7 | 1 | 2 | 1 | 51 | 42 | 3 | 8 |
| 10.06.93 | 4.5 | 158 | 0.9 | 5.0 | 1 | 3 | 1 | 50 | 42 | 4 | 12 |

TABLE 13-continued

Dynamics of peripheral blood indices in male patient G.

| Date | Erythro-cytes, $10^{12}$/l | Hemo-globin, g/l | Color index | Leuko-cytes, $10^9$/l | Baso-phils, % | Eosino-phils, % | Related to slab neutro-phils, % | Segment-nuclear, % | Lympho-cytes, % | Mono-cytes, % | S. R., mm/hr |
|---|---|---|---|---|---|---|---|---|---|---|---|
| 17.06.93 | 4.2 | 136 | 0.9 | 4.4 | | 2 | 2 | 51 | 38 | 6 | 13 |
| 08.07.93 | 4.6 | | | 5.5 | | 2 | 1 | 50 | 43 | 4 | 8 |
| 27.07.93 | | | | 5.7 | | 2 | 1 | 36 | 53 | 8 | 17 |
| 01.08.93 | | | | 3.9 | | 3 | 1 | 46 | 49 | 1 | 15 |
| 02.09.93 | 5.2 | 155 | 0.9 | 7.8 | 1 | 2 | 1 | 31 | 64 | 1 | 6 |
| 14.09.93 | 5.0 | 151 | | 8.3 | | 10 | 3 | 52 | 33 | 2 | 17 |
| 16.09.93 | 5.1 | 150 | 0.9 | 8.0 | | 8 | 1 | 50 | 38 | 3 | 18 |
| 21.09.93 | 5.0 | 150 | 0.9 | 5.8 | | 2 | 2 | 59 | 33 | 4 | 6 |

TABLE 14

Dynamics of immune indices in male patient G.

| Date | CD3+ | CD4+ | CD8+ | HLADR | CD4+/CD8+ | SIg |
|---|---|---|---|---|---|---|
| 04.05.93 | 742 | 571 | 586 | 246 | 0.97 | 244 |
| | 35.4 | 25.5 | 26.2 | 11.0 | | 10.9 |
| 01.06.93 | 627 | 280 | 209 | 308 | 1.34 | 198 |
| | 45.8 | 20.5 | 15.3 | 22.5 | | 14.5 |
| 08.06.93 | 670 | 448 | 238 | 103 | 1.84 | 115 |
| | 33.2 | 22.2 | 11.8 | 5.3 | | 5.7 |
| 10.06.93 | 651 | 485 | 256 | 218 | 1.84 | 105 |
| | 31.0 | 23.1 | 12.2 | 10.4 | | 5.0 |
| 17.06.93 | 543 | 456 | 238 | 226 | 1.9 | 318 |
| | 31.7 | 26.6 | 13.9 | 13.2 | | 21.3 |
| 08.07.93 | 868 | 348 | 319 | 726 | 1.08 | 610 |
| | 36.7 | 14.7 | 13.5 | 30.8 | | 25.8 |
| 27.07.93 | 634 | 797 | 838 | 326 | 0.94 | 519.6 |
| | 21.0 | 26.4 | 27.8 | 10.8 | | 17.2 |
| 05.08.93 | 585 | 420 | 155 | 483.5 | 2.77 | 189 |
| | 30.6 | 22.0 | 8.1 | 25.3 | | 9.9 |
| 02.09.93 | 1870 | 1227 | 1110 | 613.5 | 1.01 | 1065 |
| | 65 | 24.2 | 21.0 | 21.1 | | 21.8 |
| 14.09.93 | 972 | 789 | 597 | 446 | 1.32 | 828 |
| | 35.5 | 28.8 | 21.8 | 16.3 | | 30.2 |
| 16.09.93 | 976 | 623 | 690 | 748 | 0.9 | 472 |
| | 32.1 | 20.5 | 22.7 | 24.6 | | 15.8 |
| 21.09.93 | 523 | 275 | 599 | 530 | 0.46 | 281 |
| | 27.3 | 14.4 | 31.3 | 27.7 | | 14.7 |

TABLE 15

Dynamics of biochemical indices in male patient G.

| Date | Bilirubin total | indirect | ALT | Thymol test | Total protein | Albumin | $\alpha_1$ | $\alpha_2$ | $\beta$ | $\gamma$ |
|---|---|---|---|---|---|---|---|---|---|---|
| 07.06.93 | 7.0 | 7.0 | 0.14 | 8.0 | 86.4 | 50.9 | 7.2 | 8.4 | 12.5 | 21.0 |
| 08.07.93 | 18.72 | 18.72 | 0.11 | 5.5 | | | | | | |
| 27.07.93 | 9.36 | 9.36 | 0.42 | 2.0 | 80.8 | 53.5 | 7.0 | 8.0 | 9.5 | 22.0 |
| 02.09.93 | 12.0 | 12.0 | 0.2 | 1.5 | 72.4 | 59 | 4.0 | 9.0 | 10.0 | 18.0 |
| 14.09.93 | 3.0 | 3.0 | 0.11 | 3.5 | | | | | | |

TABLE 16

Dynamics of analyses of the urine in male patient G.

| Date | Color | Transparency | Reaction | Density | Protein | Sugar | Leuko-cytes | Erythro-cytes |
|---|---|---|---|---|---|---|---|---|
| 02.06.93 | L/yellow | Transparent | Acidic | 1016 | Traces | — | 3–4 | 0–1 |
| 17.06.93 | L/yellow | Transparent | Acidic | 1021 | — | — | 3 | — |
| 08.07.93 | Yellow | Transparent | Acidic | 1014 | — | — | 5–6 | 0–1 |
| 03.09.93 | Yellow | Transparent | Acidic | 1013 | — | — | 0–1 | — |
| 15.09.93 | Yellow | Transparent | Acidic | 1013 | 0.033 | — | 4–5 | 0–1 |

TABLE 17

Immunofermental diagnostics in male patient G.

| Date | Ag p24 | Titer AT to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 23.09.93 | − | 1:2921.5 | + | + | 1:6400 | 1:800 | 1:200 | − | + | − |
| 26.10.93 | − | 1:2771.3 | + | + | 1:8000 | not studied | + | − | + | − |

TABLE 18

Immunoblotting in male patient G.

| Date | gp 160 | gp 120 | p 65 | p 55 | p 51 | gp 41 | p 31 | p 24 | p 18 |
|---|---|---|---|---|---|---|---|---|---|
| 27.10.93 | + | + | + | + | + | + | + | + | + |

EXAMPLE 5

Male patient 930024 "D" was admitted to the AIDS Department of the Kiev Research Institute for Epidemiology and Infectious Diseases on Aug. 27, 1993.

Diagnosis: clinical AIDS; generalized lymphodenopathy, oral cavity candidiasis; intestine lambliasis; enteritis of Proteus etiology; hypochromic anemia.

The patient was revealed to be HIV infected in 1993, on occasion of a long-term (3 months) fever of up to 38 to 38.5° C., that could not be treated with the use of antibiotics (the patient was treating himself), and diarrhea of the same duration; all this caused HIV testing.

During admittance, the patient complained considerable weakness, sweating, body temperature increase of up to 39° C., headache, bad sleep, water stools 4 times a day. During the last several months the patient lost 10 kg of the body weight.

Objectively: intugements were pale. Peripheric lymph nodes: movable, painless, of elastic consistence; posterocervical—multiple, up to 0.5 cm in diameter, axillary—in groups of 3 to 5, up to 1 cm in diameter; inguinal, up to 0.5 cm.

Cardiac sounds were moderately weak and rhythmic; tachycardia. Respiration in lungs was vesicular, no rale auscultated. The abdomen was soft and painless. Liver edge was protruding from beyond the costal arch by 2 cm. No peripheric edemas were found.

Roentgenography of thorax organs, taken on Aug. 28, 1993: infiltrative changes in the upper lobe of left lung against the background of expressed bronchovascular pattern. The left root is expanded and structureless. Conclusion: pneumonia with localization in the upper lobe of left lung.

Examination by otolaryngologist: chronic subatrophic pharyngitis.

Treatment prescribed: cefasolin, biceptol, retrovir, metronidasol.

In spite of the therapy, the fever did not decrease; diarrhea continued; weakness increased; anemia progressed; lymph nodes got bigger.

Diagnosis: clinical AIDS; septic state.

On Sep. 12, 1993, the patient was subjected to administration of Medicinal preparation in an amount of 4, amount of nucleated cells being $110*10^6$/ml, CFU GM $-39*10^3$/ml, CFU GEMM $-2.0*10^3$/ml, CD. $-1.5*10^6$/ml). Method of administration: intraperitoneal.

After transplantation, the general state of the patient somewhat improved. The temperature decreased down to subfebrile values; intoxication phenomena, weakness and sweating diminished, sleeping normalized.

Table 19 through 24 show results of laboratory and immunologic tests.

By request of the patient, he was discharged. Pneumonia was gone during a month. At present, the patient's state is satisfactory, he continues taking retrovir.

TABLE 19

Dynamics of peripheral blood indices in male patient D.

| Date | Erythrocytes, $10^{12}$/l | Hemoglobin, g/l | Color index | Leukocytes, $10^9$/l | Basophils, % | Eosinophils, % | Related to slab neutrophile, % | Segment-nuclear, % | Lymphocytes, % | Monocytes, % | S.R., mm/hr | Thrombocytes, $10^9$/l |
|---|---|---|---|---|---|---|---|---|---|---|---|---|
| 31.08.93 | 3.5 | 97 |  | 6.0 | 1 | 3 | 4 | 72 | 19 | 1 | 35 |  |
| 02.09.93 | 3.4 | 95 | 0.9 | 9.8 | 1 | 3 | 3 | 72 | 18 | 3 | 45 | 347 |
| 09.09.93 | 3.4 | 98 | 0.8 | 10.2 |  | 3 | 4 | 76 | 13 | 4 | 65 |  |
| 10.09.93 | 3.5 | 95 | 0.8 | 9.6 |  |  |  |  |  |  | 48 | 280 |
| 21.09.93 | 4.4 | 110 | 0.8 | 8.6 | — | 2 | 1 | 67 | 24 | 6 | 30 |  |
| 28.09.93 | 4.7 | 120 | 0.8 | 8.3 | — | 2 | 1 | 67 | 27 | 4 | 30 |  |
| 30.09.93 | 4.5 | 110 | 0.8 | 8.7 | — | 2 | 2 | 71 | 20 | 5 | 60 |  |

TABLE 20

Dynamics of biochemical indices in male patient D.

| Date | Bilirubin total | indirect | Thymol test | ALT | Total protein | Albumin | $\alpha_1$ | $\alpha_2$ | $\beta$ | $\gamma$ |
|---|---|---|---|---|---|---|---|---|---|---|
| 31.08.93 | 9.3 | — | 1.0 | 0.11 | 69.6 | 41 | 7 | 12 | 18 | 22 |
| 02.09.93 | 5.6 | — | 1.0 | 0.22 | 72.4 | 44 | 8 | 10 | 18 | 20 |
| 09.09.93 | 19.9 | 10.2 | 0.5 | 0.22 | 72.4 | 30 | 11 | 13 | 15 | 31 |
| 23.09.93 | 3.8 | — | 1.5 | 0.39 | 69.6 | 44 | 8 | 10 | 17 | 21 |
| 30.09.93 | 7.0 | — | 1.0 | 0.39 | 66.9 | 35.3 | 7.8 | 9.4 | 16.0 | 31.5 |

TABLE 21

Dynamics of analyses of the urine in male patient D.

| Date | Color | Reaction | Density | Transparency | Protein | Sugar | Leuko-cytes | Erythro-cytes | Cylinders hyal. | Cylinders gran. | Salts |
|---|---|---|---|---|---|---|---|---|---|---|---|
| 30.08.93 | saturated | Acidic | 1015 | Turbid | 0.66 | — | 3–5 | 0–1 | 0–1 | 0–1 | oxalate |
| 07.09.93 | L/yellow | Acidic | 1015 | Transparent | 0.33 | — | 1–3 | — | 0–1 | | |
| 09.09.93 | L/yellow | Acidic | 1011 | Turbid | 0.165 | — | 2–3 | 0–1 | 0–1 | 0–1 | |
| 14.09.93 | L/yellow | Acidic | 1008 | Transparent | 0.33 | — | 5–6 | — | 2–3 | 1–2 | |
| 30.09.93 | L/yellow | Acidic | 1020 | Transparent | 0.165 | — | 8–10 | 0–1 | 1–2 | | |

TABLE 22

Dynamics of immune indices in male patient D.

| Date | CD3+ | CD4+ | CD8+ | HLADR | CD4+/CD8+ | SIg |
|---|---|---|---|---|---|---|
| 31.08.93 | 421 | 282 | 399 | 323 | 0.66 | 429 |
|  | 36.9 | 24.7 | 35 | 28.3 |  | 37.6 |
| 09.09.93 | 491 | 221 | 353 | 260 | 0.63 | 309 |
|  | 37.0 | 16.7 | 26.6 | 19.6 |  | 23.3 |
| 21.09.93 | 464 | 431 | 431 | 297 | 1.0 | 479 |
|  | 22.5 | 20.9 | 20.9 | 14.4 |  | 23.2 |
| 27.09.93 | 283 | 93.5 | 93.5 | 697 | 2.28 | 120 |
|  | 30.0 | 9.9 | 9.9 | 7.8 |  | 12.7 |
| 07.10.93 | 299 | 310 | 310 | 199 | 0.6 | 343 |
|  | 31.6 | 32.8 | 32.8 | 21.1 |  | 36.3 |

TABLE 23

Immunofermental diagnostics in male patient D.

| Date | Titer AT |
|---|---|
| 02.09.93 | 1:102400 |
| 22.09.93 | 1:6400 |

TABLE 24

Immunoblotting in male patient D.

| Date | gp 160 | gp 120 | p 65 | p 55 | p 53 | gp 41 | p 31 | p 25 | p 18 |
|---|---|---|---|---|---|---|---|---|---|
| 01.09.93 | + | + | + | − | weak | + | + | + | + |

EXAMPLE 6

Female patient 91005 "N", 25 years old, was admitted to the AIDS Department of the Kiev Research Institute for Epidemiology and Infectious Diseases on Apr. 21, 1993.

Diagnosis: clinical AIDS; pneumocystic pneumonia in the reconvalescence stage; candidiasis of oral and bronchi mucous membranes; allergic blepharoconjunctivitis; chronic hepatitis with transfer to cirrhosis; portal hypertensin; ascites; hepatolienal sybdrome.

HIV infection was diagnosed in 1989; the patient was treated in Moscow, received azidotimidin.

Since Dec. 15, 1991, the patient has been under observation at the AIDS Department.

From Nov. 11 till Dec. 22, 1992, she was treated at the AIDS Department with the following diagnosis: AIDS; pneumocystic pneumonia. From Nov. 24 till Dec. 22, 1992, asidotimidin therapy was applied with the daily dosage of 1000 mg; during patient's discharge from the hospital, she was recommended to keep on taking 500 mg/day for two weeks.

From Jan. 31 till Mar. 16, 1993, the patient was treated at the AIDS Department. She was taking retrovir from Feb. 18, 1993 till Mar. 16, 1993, in a daily dosage of 500 mg, and was discharged with recommendations to keep on taking retrovir in a daily dosage of 500 mg for several weeks. During the period of retrovir therapy, her general state improved (cough diminished, body weight increased by 4 to 5 kg); cell immunity parameters also improved.

During her admittance on April 21, 1993, the patient complained weakness, dry cough, aching pain in the right hypochondrium, periodic nasal bleeding, tongue burning, undue fatiguability, throat pain in swallowing, eye burning.

Objectively: relatively satisfactory general state; intugements without any peculiarities. Palpated peripheric lymph nodes: submandibular and posterocervical: in the shape of chains of up to 0.5 cm in diameter; axillary, in groups of 3 to 5 and 0.7 to 1.0 cm in diamater; all the nodes were of elastic consistence, mobile and painless.

Cardiac sounds were moderately weak and rhythmic with systolic murmur at the apex. Respiration in lungs was vesicular. The abdomen was soft and sensitive in the right hypochondrium, its volume being somewhat increased because of ascites. Liver edge was protruding from beyond the costal arch by 5 cm. A big and dense spleen was palpated.

On May 3, 1993, the patient was subjected to administration of Medicinal preparation in an amount of 2 ml, (amount of nucleated cells being $28*10^6$/ml, CFU GM—$44*10^3$/ml, CFU GEMM—$2.4*10^3$/ml, CD34—$1.8*10^3$/ml). Improvement of appetite was noted; the patient felt better; after one weak the pain in throat caused by swallowing, as well as burning in eyes and on tongue disappeared, weakness decreased, skin color improved.

After administration of Medicinal preparation, improvement of appetite was noted; the patient felt better.

On May 26, 1993, the patient was discharged in the satisfactory state; she categorically refused to take retrovir any more.

Tables 25 through 30 give the results of laboratory and immunologic tests.

Observation is still going on.

TABLE 25

Dynamics of peripheral blood indices in female patient N.

| Date | Erythrocytes $10^{12}$/l | Hemoglobin, g/l | Color index | Leukocytes, $10^9$/l | Basophils, % | Eosinophils, % | Related to slab neutrophile, % | Segmentnuclear, % | Lymphocytes, % | Monocytes, % | S.R. mm/hr |
|---|---|---|---|---|---|---|---|---|---|---|---|
| 16.11.92 | 4.0 | 124 | 0.9 | 5.6 | 1 | 2 | 1 | 49 | 50 | 4 | 42 |
| 09.12.92 | 3.8 | 114 | 0.9 | 6.0 | | 1 | 1 | 26 | 68 | 4 | 60 reticulocytes 10%, thrombocytes, 220 $10^9$/l |
| 02.02.93 | 3.9 | 127 | 0.9 | 8.9 | | 1 | 1 | 33 | 61 | 4 | 53 |
| 05.01.93 | 3.9 | 128 | 0.9 | 4.7 | | 2 | 1 | 45 | 48 | 4 | 45 |
| 12.04.93 | 4.0 | 121 | 0.9 | 7.6 | | 1 | 1 | 40 | 53 | 5 | 47 |
| 10.05.93 | 4.0 | 126 | 0.9 | 4.0 | | 2 | 1 | 46 | 49 | 2 | 45 |
| 24.05.93 | 4.1 | 133 | 0.9 | 4.0 | | 2 | 2 | 40 | 53 | 3 | 48 |

TABLE 26

Dynamics of immune indices in female patient N.

| Date | CD3+ | CD4+ | CD8+ | HLADR | CD4+/CD8+ | SIg |
|---|---|---|---|---|---|---|
| 18.11.92 | 21.3 | 14.4 | 22.0 | 26.4 | 0.65 | 4.7 |
| | 596 | 403 | 616 | 7393 | | 132 |
| 09.12.92 | 21.3 | 15.7 | 12.0 | 7.5 | 1.3 | 8.7 |
| | 1114 | 640 | 490 | 306 | | 355 |
| 01.02.93 | 48.3 | 13.3 | 56.0 | 9.5 | 0.2 | 6.8 |
| | 2623 | 722 | 2257 | 383 | | 369 |
| 01.03.93 | 75.2 | 10.9 | 66.0 | 6.1 | 0.17 | 5.4 |
| | 1697 | 246 | 1489 | 138 | | 122 |
| 12.04.93 | 56.0 | 13.4 | 42.7 | 11.1 | 0.31 | 11.4 |
| | 2240 | 539 | 1708 | 444 | | 456 |
| 10.05.93 | 56.5 | 5.5 | 35.0 | 35.2 | 0.16 | 21 |
| | 1107 | 108 | 686 | 690 | | 49 |
| 24.05.93 | 66.5 | 8.3 | 56.2 | 39.7 | 0.15 | 2.6 |
| | 1410 | 176 | 1191 | 842 | | 55 |

TABLE 27

Dynamics of biochemical indices in female patient N.

| Date | Bilirubin total | direct | Thymol test | ALT | Total protein | Albumin | $\alpha_1$ | $\alpha_2$ | $\beta$ | $\gamma$ |
|---|---|---|---|---|---|---|---|---|---|---|
| 12.04.93 | 4.68 | — | 12.0 | 0.79 | 86.4 | 34.1 | 4.2 | 6.4 | 12.4 | 42.9 |
| 24.05.93 | 18.72 | — | 9.5 | 0.71 | 94.8 | 40.6 | 5.1 | 6.3 | 13.9 | 34.1 |

TABLE 28

Dynamics of analyses of the urine in female patient N.

| Date | Color | Reaction | Density | Protein | Leuko-cytes | Erthyo-cytes |
|---|---|---|---|---|---|---|
| 11.04.93 | Yellow | Acidic | 1022 | 0.099 | 4–5 | 0–1 |
| 18.05.93 | Yellow | Acidic | 1020 | None | 3–5 | 0–1 |
| 23.05.93 | Yellow | Acidic | 1016 | 0.033 | 1–0 | 0–1 |

TABLE 29

Immunofermental diagnostics in femal patient N.

| Date | Ag p24 | Titer AT to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 16.11.92 | + | 1:5 | + | + | 1:12800 | 1:320 | + | neg | + | not studied |
|  | % of vironeutral AT verus Ag p24: 78% | | | | | | | | | |
| 01.02.93 | – | 1:8.1 | + | + | 1:32000 | 1:1600 | + | neg. | + | – |
|  | % of vironeutral AT versus AT: not studied | | | | | | | | | |
| 12.04.93 | – | 1:5.0 | + | + | 1:16000 | 1:800 | + | – | + | – |

TABLE 30

Immunoblotting in female patient N.

| Date | gp 160 | gp 120 | p 68 | p 55 | p 52 | gp 41 | p 34 | p 25 | p 18 |
|---|---|---|---|---|---|---|---|---|---|
| 17.11.92 | + | + | + | + | + | + | + | + | + |
| 14.04.93 | + | + | + | + | + | + | + | + | + |

EXAMPLE 7

Male patient 930009 "V", 41 years old, was admitted to the AIDS Department of the Kiev Research Institute for Epidemiology and Infectious Diseases on Mar. 24, 1993.

Diagnosis: clinical AIDS; disseminated pulmpnary tuberculosis; candidiasis of the oral cavity and intestine.

HIV infection was revealed in March, 1993. Since the end of December, 1992, the patient feels general weakness, headache, temperature increase of up to 37.3 to 38° C., pain in the joints of lower extremities and crus muscles, aches and pains in all the bones and joints, chilling.

For the first time he saw a physician on Feb. 2, 1993; the diagnosis was polyarthritis.

On Feb. 2, 1993, the patient was consulted by a hematologist: attention should be drawn to increased liver and spleen. The patient has to be examined for chronic hepatitis and manifestations of hypersplenism (Hb, 96 g/l; thromb., $124*10^9$/l).

The patient was taking ascorbic acid; folic acid; vitamins B1, B6, and B12; nicotinic acid; splenin, analgin, indometacin.

Blood count, Mar. 2, 1993: Hb, 105 g/l; Er, $3.8'10^{12}$/l; CI, 0.9; thrombocytes, $135'10^9$/l; S. R., 5 mm/hr.

Since Mar. 4, 1993, the patient was taking prednisolon. After the beginning of this treatment course, he noted improving state (decrease of pain and the feeling of tied-down joints). Since Mar. 28, 1993, the patient was taking retrovir, and since Apr. 6, 1993, Biceptol (intravenously).

Roentgenography of thorax organs, taken on Apr. 7, 1993: multiple focal shades of infiltrative nature over the total length of lungs, against the background of pneumosclerosis; expanded roots.

Conclusion: microfocal pneumonia has to be differentiated from the focal tuberculosis of the lungs.

After the consultation provided by a phthisiologist, antituberculosis therapy was prescribed, i.e. rifampicin, etambutol, isoniasid, streptomycin. On Apr. 21, 1993, the body temperature decreased and was subsequently within 36.4 to 36.8° C.

This temperature decrease was accompanied by the general state improvement, i.e. disappearance of dyspnea, decrease of cough and weakness. At the same time, aching pain in joints, hands in particular, periodic nausea, headache, vertigo, and quick fatiguability still remained.

In June 1993, dyspnea and sweating appeared again; temperature became up to 37.5° C.; acute weakness was noted.

15.07.93. Medicinal preparation was administered intraosteally, in an amount of 4 ml (amount of nucleated cells being $142*10^6$/ml, CFU GM—$64*10^3$/ml, CFU GEMM—$1.3*10^3$/ml, $CD3_4$-$1.8*10^6$/ml).

The patient endured administration of Medicinal preparation satisfactorily, though the next morning the body temperature increased up to 37.2° C. By the same evening, the temperature normalized. On Jul. 17, 1993, the patient started receiving antituberculosis therapy. In the morning of Jul. 20, 1993, the body temperature increased up to 38° C., cutis hyperemia of forearms and lower extremities, accompanied by itch, appeared (total blood count: 9% eosinophils). On the next day after taking diasolin, the state normalized.

On Jul. 27, 1997, the patient noted satisfactory state for the first time since his admittance to the hospital. Headache, nausea and fatiguability decreased; pain in joints and right hypochondrium disappeared; temperature normalized; appetite improved; the patient was able to perform physical work.

During subsequent two months noted against the background of antituberculosis therapy was gradual improvement: decrease of cough and dyspnea, normalization of temperature, improvement of appetite, decrease of weakness, much less frequent pain in muscles and joints. Blood tests carried out during two months indicated an increase in the amount of erythrocytes from 3.7 up to 4.2 O/l, increase of hemoglobin from 110 up to 132 g/l, increase of general amount of leukocytes from 2.5 up to 3.5 g/l, increase of ESR from 40 up to 26 mm/hr; absolute amount of CD4+ lymphocytes increase from 85 up to 295 cells/mm³.

On Sep. 10, 1993, the patient was discharged from the hospital in satisfactory condition and with recommendations to continue antituberculosis therapy.

Tables 31–36 give the results of laboratory and immunologic studies.

EXAMPLE 8

Female patient K., 30 years old, in which HIV infection was detected in 1986 (heterosexual way of infection). Diagnosis: HIV infection; chronic relapsing simple herpes; oral candidiasis; cryptosporidiosis. The patient complained substantial weakness, vertigo, loss of appetite, diarrhea, and considerable loss of weight. She was subjected to antiretroviral therapy, however, after 2 months her general condition became much worse, and amount of CD4+ lymphocytes decreased from 40 down to 8 cells/mm Fist treatment session with the use of the inventive Medicinal preparation was carried out on May 14, 1996. Preparation was administered intravenously in drops (0.5 ml).

During next several days, the patient noted substantial improvement of general condition, energy and spirits, appetite and sleek. In the course of two weeks, amount of CD4+ lymphocytes increased up to 40 cells/mm$^3$; general condition however worsened again (the patient complained loss of appetite, weakness, fatigue, permanent erethism). The decision was made to carry out repeated administration of Medicinal preparation (2.0 ml) on May 30, 1996 also intravenously in drops. The patient noted substantial improvement of appetite, sleep, spirits, and decrease of erethism 4nd depression. Two weeks later amount of CD4+ lymphocytes increased up to 174 cells/mm$^3$. Manifestation of diarrhea substantially decreased, unstable stools usually occurred after diet errors. The patient was discharged in satisfactory state.

During subsequent 6 months, Medicinal preparation was administered to the patient two more times. Noted was short-time subjective improvement, the general condition however remained because of permanent diarrhea associated with cryptosporidiosis. The patient died from cachexia syndrome.

TABLE 31

Dynamics of peripheral blood indices in male patient V.

| Date | Erythrocytes, $10^{12}/l$ | Hemoglobin, g/l | Color index | Leukocytes, $10^9/l$ | Basophils, % | Eosinophils, % | Related to slab neutrophile, % | Segmentnuclear, % | Lymphocytes, % | Monocytes, % | S.R. mm/hr | Thrombocytes |
|---|---|---|---|---|---|---|---|---|---|---|---|---|
| 15.03.93 | 4.4 | 139 | 0.9 | 4.5 | 1 | 1 | 2 | 58 | 34 | 4 | 14 | |
| 24.03.93 | 4.4 | 138 | 0.9 | 5.2 | | 2 | 1 | 56 | 36 | 5 | 13 | |
| 12.04.93 | 4.2 | 132 | 0.9 | 6.0 | 1 | 2 | 1 | 56 | 38 | 2 | 46 | 240 $10^9/l$ |
| 18.04.93 | 4.1 | 131 | 0.9 | 8.6 | | | 1 | | | | 60 | |
| 26.04.93 | 4.2 | 129 | 0.9 | 3.9 | 1 | 1 | 1 | 43 | 50 | 4 | 60 | |
| 17.05.93 | 4.3 | 133 | 0.9 | 4.1 | | 2 | 1 | 44 | 49 | 4 | 38 | |
| 02.06.93 | 4.1 | 132 | 0.9 | 4.0 | 1 | 2 | 1 | 34 | 58 | 4 | 50 | |
| 26.06.93 | 4.3 | 132 | 0.9 | 2.1 | | 2 | 2 | 36 | 56 | 4 | 25 | |
| 04.07.93 | 3.7 | 108 | 0.9 | 1.9 | | | | | | | 18 | 160 $10^9/l$ |
| 07.07.93 | 3.7 | 112 | 0.9 | 2.4 | | | | | | | 27 | |
| 14.07.93 | 3.7 | 110 | 1.0 | 2.5 | 1 | 2 | 2 | 13 | 78 | 4 | 40 | |
| 21.07.93 | 4.0 | 96 | 0.7 | 3.2 | 1 | 9 | 1 | 40 | 46 | 4 | 40 | |
| 02.08.93 | 3.8 | 108 | 0.8 | 2.5 | | 5 | 1 | 43 | 41 | 9 | 23 | |
| 09.08.93 | 4.0 | 124 | 0.9 | 3.7 | | 13 | 1 | 42 | 41 | 3 | 45 | |
| 05.09.93 | 4.2 | 122 | 0.9 | 3.7 | 1 | 4 | 2 | 52 | 38 | 3 | 26 | |

TABLE 32

Dynamics of immune indices in male patient V.

| Date | CD3+ | CD4+ | CD8+ | HLADR | CD4+/CD8+ | SIg |
|---|---|---|---|---|---|---|
| 15.03.93 | 21.3 | 14.4 | 22.0 | 26.4 | 0.65 | 4.7 |
| | 596 | 403 | 616 | 7393 | | 132 |
| 12.04.93 | 273 | 15.7 | 12.0 | 7.5 | 1.3 | 8.7 |
| | 1114 | 640 | 490 | 306 | | 355 |
| 17.05.93 | 48.3 | 13.3 | 56.0 | 9.5 | 0.2 | 6.8 |
| | 2623 | 722 | 2257 | 383 | | 369 |
| 14.07.93 | 75.2 | 10.9 | 660 | 6.1 | 0.17 | 5.4 |
| | 1697 | 246 | 1489 | 138 | | 122 |
| 28.07.93 | 56.0 | 13.4 | 42.7 | 11.1 | 0.31 | 11.4 |
| | 2240 | 539 | 1708 | 444 | | 456 |

TABLE 33

Dynamics of biochemical indices in male patient V.

| Date | Bilirubin total | direct | indirect | Thymol test | ALT | Total protein | Albumin | $\alpha_1$ | $\alpha_2$ | $\beta$ | $\gamma$ |
|---|---|---|---|---|---|---|---|---|---|---|---|
| 05.04.93 | 7.0 | None | 7.0 | 2.0 | 0.11 | 61.2 | 42.9 | 8.5 | 10.9 | 15.8 | 21.5 |
| 17.05.93 | 9.36 | — | 9.36 | 7.0 | 0.11 | 61.2 | 45.0 | 6.5 | 7.8 | 15.7 | 25.0 |
| 02.06.93 | 4.68 | — | 4.68 | 4.0 | 0.15 | 66.9 | 41.1 | 6.4 | 7.4 | 17.7 | 27.4 |
| 28.06.93 | | | | | | 75.2 | 48.4 | 3.8 | 6.3 | 13.8 | 27.7 |

TABLE 34

Dynamics of analyses of the urine in male patient V.

| Date | Color | Reaction | Density | Transparency | Protein | Sugar | Leuko-cytes | Erthyo-cytes |
|---|---|---|---|---|---|---|---|---|
| 24.02.93 | Yellow | Acidic | — | Transparent | — | — | 7–8 | 0–1 |
| 15.03.93 | L/yellow | Acidic | 1010 | Transparent | — | — | 1–3 | 0–1 |
| 26.04.93 | Yellow | Acidic | — | Transparent | 0.132 | — | 3–5 | 0–1 |
| 11.05.93 | Yellow | Acidic | 1011 | Transparent | — | — | 2–3 | 0–1 |
| 24.05.93 | Yellow | Acidic | 1012 | Transparent | — | — | 1–2 | single |
| 23.06.93 | Yellow | Acidic | 1011 | Transparent | — | — | 1–3 | 0–1 |
| 14.07.93 | Yellow | Acidic | 1009 | Transparent | Traces | — | 1–2 | 0–1 |

TABLE 35

Immunofermental diagnostics in male patient V.

| Date | Ag p24 | Titer to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 15.03.93 | neg. | 1:20.4 | + | + | 1:32000 | neg. | + | − | + | − |
| 28.06.93 | neg. | 1:12.4 | + | + | 1:32000 | not studied | + | − | + | − |
| 17.06.93 | neg. | 1:10.8 | ++ | ++ | 1:16000 | not studied | + | − | + | − |

TABLE 36

Immumoblotting in male patient V.

| Date | gp 160 | gp 120 | p 65 | p 55 | p 51 | gp 41 | p 31 | p 24 | p 18 |
|---|---|---|---|---|---|---|---|---|---|
| 16.03.92 | + | + | + | − | + | + | + | + | − |

Pharmacologic properties

Therapeutic effects attained through application of the inventive medicinal preparations do not involve implantation of cells but are rather associated with:
- restoration of the functional activity of immunity through administered Medicinal preparation;
- outside replenishment of resources required for production of important components of the immune system;
- replenishment of the pool of stem and progenitor cells that are initial for immune functions;
- overcoming of infectious complications;
- a decrease in the manifestation of neurologic symptomatology;
- recovery of content of erythrocytes, leukocytes, platelets;
- deminising of neurological symptomatic and partial recovery of nerve system functions;
- optimization of the psychologic and psychophysiologic state of a patient.

Manifestation, by the medicinal preparation, of the complex effect consisting in:
- restoration of immune indices (total amount of leukocytes and lymphocytes, including subpopulations of CD4, CD3, CD8)
- normalization of blood indices (leukocytes, erytrocytes, thrombocytes) whose drop is associated, inter alia, with application of antiviral preparations
- decrease in infectious complications
- correction of damages to the nervous system, decrease in the peripheral neuropathy, decrease in manifestations of neurologic symptomatology, dementia;
- removal of the astheno-neurotic syndrome,
- improvement of general state of patients, reduction of weakness and sweating,
- improvement of appetite, weight gain, expansion of the locomotive conditions
- improvement of mental and physical work capacity
- optimization of the psychoemotional state, decrease of depression symptoms,
- substantial softening of the progress of disease
- decrease in the rate of disease progress
- improving of the quality of life Pharmacokinetics of Medicinal preparation We have described regularities of reactions and clinical patterns that are observed in patients upon administration of Medicinal preparation.

The whole process of preparation effect can be divided into two separate stages that differ in time and clinical symptoms.

The first stage that lasts for about one month includes early clinical symptoms manifested during initial hours after administration and may have either increasing or undulating nature. It is early improvement syndrome manifested in the form of improvement of general condition and appetite, temperature drop, decrease in manifestation of weakness and sweating, increase in working capacity. This syndrome is the most demonstrative in patients having symptoms of grave intoxication and grave progress of disease. Observed during this stage is the syndrome of changes in psychophysical consition: decrease in depression, improvement of emotional condition, thinking processes, memory, feelings, as well as substantial growth of the will component. Also observed is the syndrome of improvement of the quality of life, which recently gets special attention in patients suffering from fatal diseases. This stage is also characterized by decrease in clinical symptoms of the disease: improvements of immune status and hemopoiesis, decrease in manifestation of basic symptoms of the disease, reduction of the general activity of inflammatory processes etc.

The second stage develops 1–2 months after administration of Medicinal preparation and consists in a gradual decrease of clinical symptoms of the disease: improvement of immune status, formation of stable hemopoiesis, decrease of inflammatory symptoms, improvement of the quality of life, increase of Karnofsky index [10].

Clinical features

Therapeutic indications

Application of Medicinal preparation is possible with any forms of HIV-disease, including HIV-infected persons, persons with prodromal lymphoadenopathy syndrome, patients with AIDS related complex, and AIDS patients.

The preparation is used in case of disease progress, in case of decrease in amounts of lymphocytes having markers such as CD4, CD3, and CD8, and the total amount of lymphocytes. The increase in amount of CD4 lymphocytes is especially considerable in case of preparation use in patients having the level of 50 . . . 400 CD4 cells/w (increase was observed in 80–90% patients from various clinical groups), as well as in patients in which an increase in amount of CD4 lymphocytes exceeds 100 cells or 50% during last three months.

The preparation is used by patients suffering from HIV infection, whose evaluation according to Karnofsky index corresponds to 70–80 points or less, as well as by persons in which a decrease in Karnofsky index amounts 20 points during last 6 months.

The preparation considerably facilitates the progress of such clinical symptoms that can be observed in HIV-disease as acute and chronic bronchitis, acute pneumonia, infections of oral mucous membranes, esophagitis, enterocolitis, meningoencephalitis, dermatitis, and other diseases caused by infection.

Medicinal preparation has the capability to restore amounts of leukocytes, erythrocytes, and thrombocytes, whose decrease has been associated with HIV infection and use of antiretroviral therapy.

Also possible is application of Medicinal preparation in patients suffering from Kaposi's sarcoma and non-Hodgkin's lymphoma, and particularly in those patients for whom systematic chemotherapy can be prescribed. In this case, the preparation may be applied prior to the beginning of treatment with chemopreparations in order to restore blood indices and patient's condition, which would result in better endurance of subsequent chemotherapy. Medicinal preparation may be used during and after chemotherapy to restore amounts of leukocytes, erythrocytes, thrombocytes, as well as for elimination of the toxic effect of chemopreparations on the internal organs (enteropathy, hepatitis, encephalopathy etc.).

The preparation provides substantial decrease in the symptoms of injuries of the nervous system, eliminates symptoms of peripheral neuropathy, reduces headache and muscular pain, restores sensor functions, decreases symptoms of focal neurologic symptoms. It stops the development of dementia and can reduce its manifestation.

The preparation reduces symptoms of the astheno-neurotic syndrome.

Medicinal preparation optimizes psychoemotional status and decreases manifestation of depression; it promotes an increase in mental and physical ability to work.

Medicinal preparation decreases symptoms of weakness, sweating; it improves appetite, stops loss of weight, and allows this weight to be increased.

The preparation may be used to restore or improve the quality of life.

In case of preparation use in persons having amount of CD4 lymphocytes of more than 400 cells/ml, it is recommended to control HIV-load and, in case of its increase, to prescribe antiretroviral therapy. It has to be noted that during the first month after administration of the preparation, HIV-load may temporarily increase and then to independently decrease down to undetectable level.

Contraindications for the use of the claimed medicinal preparation:

Preparation is not recommended for patients having amount of CD4 lymphocytes of 0 . . . 20 cells/ml and Karnofsky index of 10 to 20 points; in this case, the use of the preparation is inefficient due to a low activity of immune response and substantial disorders of homeostasis indices.

Terminal stages of the disease (pronounced intoxication, profound metabolic disorders, severe systemic decompensation).

Vasculitis in acute phase. Capillaritis, phlebitis, arthritis. The treatment is possible after achievement of remission in 2 to 3 months.

Recently revealed thrombosis. The treatment is possible after 3 to 6 months.

Recently revealed ophthalmopathies. Hemorrhages in eye tissues. The treatment is possible only 2 to 3 months after hemophthalmopathy.

Pronounced pulmonary hypertension associated with vasculitis, thrombosis, multilobular pneumonia with the development of acute or subacute cor pulmonale.

Myelocarcinosis.

Presence of a site of chronic infection. Preliminary sanation is necessary.

Side effects

1. Possible aggravation of chronic flaccid inflammatory process (chronic tonsillitis, pulpitis, paradontitis, maxillary sinusitis, ethmoiditis, cystitis etc.) during initial days upon administration of the preparation.

In case of expressed aggravation, inflammatory process is arrested by a common antiinfection therapy (antibiotics, sulfanilamides, antimycotic preparations etc.). In the course of several weeks, expression of an inflammatory process is sharply decreased.

2. In individual cases, an increase in amount of thrombocytes above 320 g/l was noted. Expression of such increase is never substantial, its duration amounting to several weeks, Clinical equivalents of thrombocytosis were not observed. Possible is prescription of antiagregant therapy, e.g. acetylsalicylic acid in a common dosage.

Special application precautions

1. Awareness of safety measures used in handling liquid nitrogen.

2. Requirement to use medical gloves. Eyes should be protected with special screens or goggles.

3. Container unfreezing should be carried out in compliance with the following rules.

Unfreezing of medicinal preparation is carried out directly before their application. Unfreezing program comprises two phases, fast and slow ones.

Material passes the fast unfreezing phase by means of placing the container into water bath at 40° C. (overheating above 42° C. isimpermissible), till occurrence of a small movable piece of ice in the center of container.

This is followed by slow phase at room temperature, till disappearance of the above piece of ice in the container that has been removed from water bath.

Unfrozen cell suspension can be stored at room temperature for not more than 2 hours.

4. Container cap should be treated with an anticeptic (e.g. 96° ethyl alcohol like in case of opening medical ampoules containing injection solutions). The content is drawn into a sterile syringe, and then transferred to a blood transfusion system.

Application duting pregnancy and breast feeding periods

We have a positive experience of applying preparations containing cell suspensions of a similar composition in females being in the second half of the pregnancy term, in order to eliminate anemic syndrome.

Special studies of the preparation in patients suffering from AIDS and in HIV-carriers during pregnancy and breast feeding periods have not been carried out (there exists only a single observation pertaining to this issue and given in Examples of the Patent Application).

Medicinal and other forms of interfaction

1. Application of the preparation is possible against the background of antiretroviral therapy, in compliance with common schemes.

2. In some patients, application of Medicinal preparation against the background of AZT delayed an increase in the total amount of lymphocytes having CD3, CD4, and CD8 markers.

3. Preparation effects may disappear upon chemotherapy (e.g. vincrystin, sysomycin), as well as with preparations of 2,4, amino quinoline series (e.g. chloroquine phosphate, delagil).

4. On the date of preparation administration, infusion therapy should not be used.

5. Parallel application of other methods of immune therapy (e.g. Gamma globulin, Gamma interferon, Interferons, Interleukin-2, Thymic factors, etc.) is not recommended.

Dosage and method of administration

The mode of administration of medicinal preparation to recipient's body in the process of treatment.

Medicinal preparation prepared from fetal liver and/or spleen are most preferably administered intravenously as demonstrated in Examples, although also possible are such modes as intra-abdominal or intraosteal (Example 1). Given below are possible specific procedures of such administration.

Medicinal preparation can be administered intravenously, in drops, in the composition of 100–150 ml of isotonic solution of sodium chloride, at a rate of 20 to 40 drops a minute.

With intra-abdominal administration, the cell suspension is diluted with isotonic solution of sodium chloride up to a total amount of 50 ml, and administered intra-abdominally, in the form of a jet.

In case where a patient has a fresh thrombus or hemophthalmopathy (hemorrhage in eye tissues), as well in cases of hypersplenism, it is expedient to use intraosteal administration of cell suspension in the chest, in an amount of up to 50 ml of isotonic solution of sodium chloride, and in the form of a jet.

The amount of administered preparation may go up to whole amount of medicinal preparation prepared from liver and spleen of one human embryo that usually does not exceed approximately 10.0 ml. Here, the quantity of utilized 2-mi containers with the preparation may vary preferably from 1 to 16. Generally, the amount of cell suspension administered during one treatment session ranges within 0.5 to 2.0 ml (1 to 3 containers).

Also possible is a combined use of medicinal preparation prepared from fetal liver and fetal spleen.

Repeated administration of preparation

In case of repeated administration of the medicinal preparation during subsequent stages of patient's treatment, preferred is application of the cell suspension prepared from the same embryo that was previously used. To implement this feature of the method of preparation of cell suspension from a fetal organ, such suspension is distributed to several containers. Embryo suspension is assigned to a specific patient and stored in the cryobank for future use with the same patient.

To authors' opinion, an advantage of the inventive method comprises the possibility of attaining full-scale therapeutic effect through application of small doses of the fetal material.

Features of the "dose" category with respect to inventive medicinal preparation.

Here, it should be noted that the "dose" category with respect to application of fetal material that is used to a high extent as an "seeding material" and provides therapeutic effect through efforts made by descendants of cells contained in administered medicinal preparation rather than by way of direct action of the administered preparation, is quite different from the dose category with respect to chemical medicines.

The term "dose" is characterized a) by an amount of administered acting matter of the medicinal preparation, and b) by a time of preparation administration (periodicity, dating for disease progress stages, depending on indices characterizing the condition of an organism).

In the medicinal preparation of the invention, i.e. cell suspension, both the acting matter and the notion of its amount feature specific meanings.

The inventive medicinal preparation comprises a cell suspension consisting of living cells. The therapeutic effect depends on single cells that are able to survive and provide posteriors, thereby becoming progenitors of clones, rather than on the number of administered cells. Majority of cells will be lost upon getting into such environment inside the recipient organism that is suitable for development. Therefore, neither the number of administered cells nor the volume of suspension comprise the acting dose of preparation. Here, "either everything or nothing" rule is acting. In case where within the treatment time anticipated for revealing of the therapeutic effect such effect does not come, the repeated treatment should be carried out. The authors have not observed any situations where the therapeutic effect would not have come at least after the third treatment, provided that previous attempts were ineffective.

In repeated treatments of the same samples of medicinal preparation, that have resulted in previous formation of a positive therapeutic effect, such positive therapeutic effect is always observed.

Selection of the amount of the inventive preparation, proposed for administration during one treatment session and amounting up to 8 ml, is caused by the following considerations. 8.0 ml is a maximum volume of cell suspension that can be prepared from the starting material to ensure the above characteristics.

The amount of administered preparation may go up to whole amount of medicinal preparation prepared from liver and spleen of one human embryo that usually does not exceed 10.0 ml. Here, the quantity of utilized 2-ml containers with the preparation may vary from 1 to 16. Generally, the amount of cell suspension administered during one treatment session ranges within 0.5 to 2.0 ml (1 to 3 containers).

As mentioned above, the amount of cell suspension administered during one treatment session usually ranges within 0.5 to 2.0 ml.

Evaluation of treatment efficiency

Evaluation of treatment efficiency is carried out with the use of common methods and includes clinical and laboratory assessments:

1. Deriving Karnofsky index from Karnofsky scale during each visit to physician.

5. Physical examination of a patient prior to and one day after application of Medicinal preparation to evaluate the expression of the early improvement syndrome in the form of change of psychophysical status, appetite improvement, sleep normalization, temperature drop, decrease in manifestation of weskness, increase of physical activity. It is recommended to repeat examination of patient after 14 to 16 days; subsequent examinations should be carried out in compliance with common schedule.

2. General blood test including identification of amounts of leukocytes, erythrocytes, thrombocytes, lymphocytes, and ESR is carried out prior to administration, two weaks and one month after administration, and then upon discretion of physician.

3. Immunologic monitoring comprises generally approved tests allowing to separate, with the use of monoclonic antibodies, subpopulations of lymphocytes and other blood cells such as $ND3^+$, $ND4^+$, $CD8^+$; calculation of CD4/CD8 ratio, and possible definition of $ND19^+$, $ND14^+$, $CD16^+$, and HLA-DR. It is recommended to carry out studies prior to administration, 14 and 30 days after/ and then in compliance with recommendations of physician.

4. Carrying out calculation of amount of the viral RNA in the blood plasma in order to select and conduct antiretroviral therapy. It is recommended to carry out studies prior to administration, 14 and 30 days after/ and then in compliance with recommendations of physician.

Overdosage.

Overdosage of Medicinal preparation is impossible.

Special warnings.

None.

Ability to affect reaction time when driving road vehicles or operating other potentially dangerous mechanisms.

During several hours upon administration of Medicinal preparation, patients may demonstrate some psychoemotional changes (moderate activation, slight euphoria), which fact gives the basis for recommendation to try not to drive road vehicles or operate other potentially dangerous mechanisms during one day after administration of the preparation.

Pharmaceutical features.

1. Forms of incompatibility.

1.1. Administration of the preparation jointly with hypotonic and hypertonic solutions is inadmissible.

1.2. Any contact between the preparation and substances having cytostatic effect should be avoided.

1.3. Possibility of preparation heating above 42° C. should be avoided.

2. Storage term.

2.1. Storage term of the preparation frozen in liquid nitrogen is indefinitely long.

2.2. In unfrozen condition, the preparation may be kept at room temperature prior to administration up to 4 hours.

3. Special storage precautions.

Container with the preparation should be stored in liquid nitrogen in submerged position (rather than in nitrogen vapor).

Preparation unfreezing and subsequent freezing for storage is inadmissible. Accidentally unfrozen preparation should not be used and has to be destroyed.

4. Description and composition of container for primary packaging.

Used for primary packaging shall be plastic containers ensuring preparation storage in liquid nitrogen (e.g. containers made of special types of polypropylene and having 1 to 5 ml capacity).

Special precautions for handling unused preparations or medicinal preparation waste.

Containers emptied of preparation, unused portion of preparation, and accidentally unfrozen preparations should be placed into special containers for infected material, from which they cannot be withdrawn. Such containers in turn should be destroyed by burning.

REFERENCES

1. Bachetta R., Vandekerckhove B. A. E., Touraine J.-L. et al. Chimerism and tolerans to host and donor in severe combined immunodeficiencies transplanted with fetal liver stem cells // J3. Clin. Invest.—1993.—N 91.—P.1067–1018.
2. Fedotenkov A. G., Shishkin I. D., Danilova L. A. et al. Cryopreservation of bone marrow at low temperature for clinical application. Problems of Hematology, 1966, vol. 0, No.2, pp.45–50.
3. Hanks' solution (Hanks, Wallace. 1949)
4. Hann V., Bodger M., Hoffbrand A. Development of pluripotent hematopoietic progenitor cells in the human fetus l/Blood.—1983.—Vol.62.-N4-P. 118–123.
5. Karnofsky D. A., Abelman W. N., Craver L. F., Burchenal J. H. The use of the nitrogen mustards in the paliative treatment of carcinoma // Cancer.—1948.—N 1.—P. 634–656.
6. Kelement E. Recovery from chronic idiopatic bone marrow aplasia of a young mother after intravenous injection of unprocessed cells from liver (and youlk sac of her 22 mm CR length (Empri O) empeyo. // Second J. Hematol.—1973, 10, N 4, p.305–308.
7. Landsdorp P. M., Dragowska W., Mayani H. Ontogeny-Related Changes in Proliferative Potential of Human Hematopoictic Cells, J.Exp.Med., 178(3):787–791, 1993.
8. Lucarelli G., Izzi T., Delfini G. Fetal liver transplantation, in severe aplastic anemia // Hematologica.—1978.—V.63, NI.—P. 93–94.
9. Lucarelli C., Izzi T., Porcelini A. Fetal liver transplantation in aplastic anemia and acute leukemia // Fetal liver transplantation.—Amsterdam etc. Exerpta med., 1980.—P. 1284–1299.
10. Smikodub A., Markov J. Philipchak O., A new method of treatment of patients with HIV // Collection of thesis of First National Scientific Practice Conference about HIV with international participation.—Kiev 1995.
11. Touraine J.-L. Fetal tissue transplantation for severe combined immunodeficiency in Europe // Exp. Hematol.—1982.—V.10, suppl.10.—P. 40–45.
12. Touraine J.-L. The Place of Fetal Liver Transplantation in the Treatment of Inborn Errors of Metabolism // J. Inher. Metab. Dis.—1991.—N14.—P. 619–626.
13. Touraine J.-L., Raudrant D., Rebaude A. In utero transplantation of stem cells in humans: immunological aspects and clinical follow up of patients // Bone Marrow Transplantation.—1992.—N 9, Suppl. 1.—P.121–126.
14. U.S. Pat. No 5,811,089 Smikodub A. I., Markov I. S., Pilipchak E. M. "Pharmaceutical preparation with immunosubstituting properties and based on a cell suspension, and a method of using the said preparation to treat acquired immune deficiency syndrome (HIV infection)."

What is claimed is:

1. A pharmaceutical composition for administration to a human having acquired immune deficiency syndrome caused by HIV-infection, which comprises:

a cell suspension from a single human embryo having a gestation of seven weeks or less wherein said cell suspension is selected from the group consisting of human hematopoietic liver cells, human hematopoietic spleen cells and a mixture of human hematopoietic liver and spleen cells; and in which the contents of nucleated cells is 5 to $200 \times 10^6$; the contents of colony-forming units of granulocyte/macrophage (CFU-GM) is 20 to $200 \times 10^3$/ml; the contents of colony-forming units of granulocyte, erythrocyte, monocytelmacrophage, megakaryocyte (CFU-GEMM) is 0.5 to $50 \times 10^3$/ml; and the contents of progenitor cells is (CD 34) 1 to $20 \times 10^6$/ml.

2. A pharmaceutical composition according to claim 1 including a therapeutically acceptable carrier and a cryo-preservative.

* * * * *